(12) United States Patent
Lewis, Jr. et al.

(10) Patent No.: US 6,780,411 B2
(45) Date of Patent: Aug. 24, 2004

(54) TISSUE SEALANT COMPOSITIONS

(75) Inventors: Kenneth B. Lewis, Jr., Seattle, WA (US); Paul A. Brown, Florence, MT (US); Gerald W. Lasser, Lynnwood, WA (US); Paul D. Bishop, Fall City, WA (US)

(73) Assignee: ZymoGenetics, Inc., Seattle, WA (US)

( * ) Notice: Subject to any disclaimer, the term of this patent is extended or adjusted under 35 U.S.C. 154(b) by 131 days.

(21) Appl. No.: 10/053,316

(22) Filed: Jan. 17, 2002

(65) Prior Publication Data

US 2002/0110554 A1 Aug. 15, 2002

Related U.S. Application Data

(63) Continuation of application No. 09/303,821, filed on Apr. 30, 1999, now abandoned.
(60) Provisional application No. 60/112,245, filed on Dec. 14, 1998, and provisional application No. 60/083,872, filed on May 1, 1998.

(51) Int. Cl.[7] ................ A61K 38/00; A61K 38/48; A61K 9/70; A61L 15/32
(52) U.S. Cl. ................ 424/94.64; 424/443; 424/444; 424/484; 514/2; 514/53; 530/381; 530/382; 530/383
(58) Field of Search ................ 424/94.64, 443, 424/444, 484; 514/2, 53; 530/381, 382, 383

(56) References Cited

U.S. PATENT DOCUMENTS 6,117,425 A * 9/2000 MacPhee et al. ........ 424/94.64

FOREIGN PATENT DOCUMENTS

WO     WO 93/05067 A1 * 3/1993
WO     WO 96/4025     7/1996

OTHER PUBLICATIONS

Lewis et al., "The use of recombinant human fibrinogen, thrombin, and factor XIII to make a fully functional fibrin sealant," Circulation 96 (8): I–352, Nov. 1997.*
Prunkard et al., "Heterologous production of recombinant human fibrinogen, thrombin, and factor XIII as components of completely recombinant fibrin sealants," Thrombosis and Haemostasis, Supp. [S], p. OC152, Jun. 1997.*
Prunkard et al., "High–level expression of recombinant human fibrinogen in the milk of transgenic mice," Nature Biotechnology, 14: 867–871, Jul. 1996.*

* cited by examiner

Primary Examiner—Scott D. Priebe
(74) Attorney, Agent, or Firm—Paul G. Lunn; Gary E. Parker

(57) ABSTRACT

Tissue sealant compositions containing human recombinant fibrinogen, human recombinant factor XIII and human recombinant thrombin. Also disclosed are preferred formulations and uses therefore.

2 Claims, 8 Drawing Sheets

TISSUE SEALANT COMPOSITIONS

This is a continuation of U.S. patent application Ser. No. 09/303,821, filed on Apr. 30, 1999, now abandoned, which claims the benefit of under 35 U.S.C. §119(e) of U.S. Provisional Application No. 60/112,245 filed on Dec. 14, 1998 and U.S. Provisional Application No. 60/083,872 filed on May 1, 1998.

BACKGROUND OF THE INVENTION

The present invention relates to recombinant human fibrin sealant (rhFS), which comprises recombinant human fibrinogen (rhFbgn), recombinant human thrombin (rhThrombin) and optionally recombinant human FXIII.

Fibrin sealant (FS) is a mixture of three protein components: Fibrinogen (Fbgn), Thrombin, and Factor XIII (FXIII). Fbgn forms the structural matrix of the sealant and is present in the largest concentration. Thrombin and FXIII are enzymes, and are present in much lower concentrations. Existing FS are prepared using Fbgn purified from human blood, and thrombin purified from either bovine or human sources. The Fbgn for commercial FS is derived from pooled plasma, but Fbgn for FS is also purified from single-donor and autologous sources by many blood banks. Regardless of the source of the components, FS are typically formulated as two solutions: Fbgn+FXIII, and Thrombin+CaCl$_2$. When mixed, the thrombin converts Fbgn to fibrin (Fbn), and polymerises to form a gel. Thrombin also converts the zymogen (inactive) form of FXIII to the active form that, in the presence of calcium, covalently cross-links the polymerised Fbn molecules to strengthen the gel and modify its physical properties (FIG. 1). When Fbgn is purified from human plasma, the FXIII is normally co-purified as a contaminant of the Fbgn. (FS prepared from blood-derived Fbgn may also contain other proteins, such as fibronectin (FN) and growth factors, as contaminants.)

DETAILED DESCRIPTION OF THE INVENTION

The present invention provides a totally recombinant Fibrin Sealant (rhFS), which comprises recombinant human Fbgn (rhFbgn), recombinant human thrombin (rhThrombin) and optionally recombinant human FXIII (rhFXIII) (zymogen or active). Recombinant human fibrin sealant (rhFS) is an alternative to existing fibrin sealants (FS) derived from non-recombinant components.

Preferred embodiments of the invention will now be described in greater detail. Reference is made to the accompanying drawings, in which:

Figure 1:
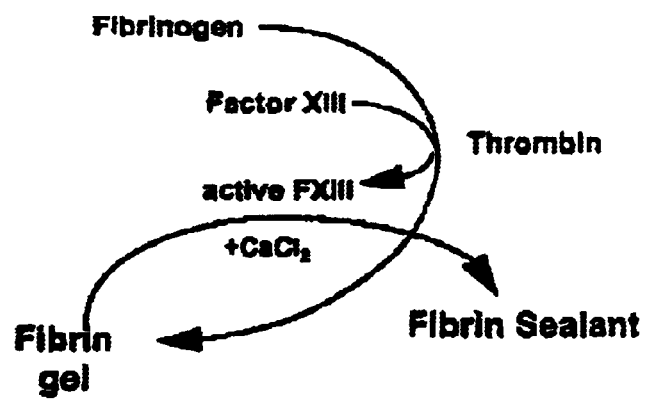
FIG. 1 shows the biochemical mechanism by which Fbgn, Thrombin, and FXIII combine to form FS.

rhFbgn for use in the invention may in principle be prepared by any suitable recombinant process. However, since typically something over 98% by weight of the protein components of a fibrin sealant will be fibrinogen, it is preferred that the rhFbgn be prepared by a process which readily allows bulk production. For this reason, the most suitable recombinant processes involve the production of rhFbgn in body fluids of transgenic animals, particularly the milk of placental mammals such as sheep, pigs, cattle, goats, rabbits and camels. A process for the production of rhFbgn in this way is disclosed in WO-A-9523868, the teaching of which is incorporated herein by reference. While it is preferred for the rhFbgn used in the invention to be composed of A$\alpha$, B$\beta$ and $\gamma$ chains having the specific sequences set out in WO-A-9523868 in SEQ IDs 1, 3 and 5, respectively, (or SEQ IDs 2, 4 and 6, respectively), allelic variation, both natural and artificial, can be tolerated, for example within the limits set out in WO-A-9523868 (at least 90%, 95% or 99% identity to corresponding natural chains, in increasing order of preference).

In human plasma, some 80% of the fibrinogen present is $\gamma$-fibrinogen, and the remaining 20% is $\gamma$'-fibrinogen, which includes the alternatively spliced $\gamma$' chain. A biological function of the $\gamma$' chain is to bind to Factor XIII, and it does so with great affinity. In the present invention, it is preferred that the rhFbgn be exclusively $\gamma$-fibrinogen, i.e. that the $\gamma$' be absent. This avoids the complexity of an additional transgene construct being present in the host animal and also side-steps the potential problem of the rhFbgn binding to Factor XIII of the host transgenic animal (for example sheep), which might otherwise be difficult to remove. Surprisingly, rhFbgn without the $\gamma$' chain is not unduly compromised, and acceptable fibrin gels can still be formed.

It has been noted that recombinant fibrinopeptide A, for example as produced in the milk of transgenic sheep, is overphosphorylated in comparison to the plasma derived molecule. Remarkably, in spite of what appears to be an inappropriate degree of phosphorylation, the recombinant fibrinopeptide A is still cleaved by thrombin, and the kinetics of cleavage rate do not appear to be materially impaired.

rhFbgn, for example as produced in the milk of transgenic sheep, appears to be undersialyated. Because of this, it may reasonably be expected that the rhFbgn would not be functional in the invention for two reasons. First, since the solubility of fibrinogen is known to depend on adequate sialyation, and as fibrinogen is in any event among the least soluble of plasma proteins, there is the real possibility that not enough soluble fibrinogen would be available in the present invention to form a fibrin gel of adequate tensile strength. Secondly, the degree of sialyation is believed to control the rate of fibrin fibre formation. In spite of these reasons for expecting failure, the present invention enables fibrin gels to be successfully made.

rhThrombin for use in the invention may also in principle be prepared by any suitable recombinant process. As it is an enzyme, it need be present in much lower amounts than rhFbgn. While a variety of hosts may be used to produce rhThrombin, the most preferred recombinant processes involve the production of rhThrombin by mammalian cells, for example CHO cells. The rhThrombin may be produced in inactive form and activated as part of the purification process. Processes for the production of rhThrombin in this way are disclosed in U.S. Pat. Nos. 5,476,777, 5,502,034 and 5,572,692, the teachings of which are incorporated herein by reference.

If included, rhFXIII for use in the invention may again in principle be prepared by any suitable recombinant process. The most preferred recombinant processes involve the production of rhFXIII by host cells which may be microbial cells, for example yeast cells, in culture. Mammalian cells may also be the host cells of choice in particualr circumstances. Processes for the production of rhFXIII in this way are disclosed in EP-A-0268772, the teaching of which is incorporated herein by reference.

In the most preferred embodiments of the invention, the recombinant human Fbgn (rhFbgn) is secreted in the milk of transgenic sheep; the recombinant human thrombin (rhThrombin) is expressed as an inactive form by CHO cells, and activated as part of the purification process; and recombinant human FXIII (rhFXIII) expressed cytoplasmically by yeast.

As a product, rhFS is free of the risk of potential human pathogens associated with blood-derived products. The recombinant proteins used is rhFS may be highly purified, and specifically assayed to ensure that contaminants derived from the host organism have been removed during processing. Recombinant production also ensures a reliable and consistent source of the three protein components. Additionally, rhFS can be formulated to optimise its functional properties for a given clinical indication(s).

rhFbgn can polymerise into a macroscopic clot or gel, and this gel is able to act as a sealant, glue, haemostat, or wound healing matrix in vitro and in vivo.

The complete characterization of an rhFS includes both the biochemical characterisation of its individual protein components and the functional charactensation of the combined product. The enzymatic components of rhFS, rhThrombin and rhFXIII, can be purified to homogeneity and accurately characterised with respect to their identity, purity, and specific activity. Consequently, their behaviour as components of rhFS is, by means of the invention, very predictable. In contrast, rhFbgn is obtained as a heterogeneous population of related species, and its behaviour as the principal component of rhFS is less predictable a priori, but can be readily characterised.

At the most elementary level, rhFbgn, as well as Fbgn purified from human plasma, is a 340 kD molecule composed of six disulphide-linked chains: two alpha, two beta, and two gamma. However, each of these six chains can be heterogeneous. The heterogeneity can be at the level of primary amino acid sequence (caused by genetic polymorphism, alternative splicing, or proteolysis) and/or at the level of post-translational modifications (such as glycosylation of the beta and gamma chains or phosphorylation of the alpha chain). The combination of six potentially heterogeneous chains into one molecule gives rise to an enormous variety of related species, all of which are identified as Fbgn.

There are several distinct differences between rhFbgn and Fbgn purified from human plasma. In plasma-derived Fbgn, there are two alternatively spliced gamma chains ($\gamma$ and $\gamma^1$), of which only the major form ($\gamma$) is present in rhFbgn. Additionally, the glycosylation of the beta and gamma chains (there is no glycosylation of the alpha chain) of rhFbgn is slightly different from that on plasma-derived Fbgn, but is similar to that found on other proteins expressed in the milk of transgenic animals. Also, the Ser3 of the alpha chain of rhFbgn is more highly phosphorylated than Ser3 of the alpha chain of plasma-derived Fbgn. (This phosphorylation does not cause any functional differences.) Finally, there are detectable differences in heterogeneity caused by C-terminal proteolysis of a number of highly protease-sensitive sites on the alpha chain. However, differences of a similar magnitude are also observed between plasma-derived Fbgn from different sources.

In practice, homogeneous Fbgn preparations can only be achieved with great difficulty, and Fbgn is normally obtained as a population of related species. If desired, several distinct Fbgn sub-populations can be partially separated based on differences in solubility and binding to ion exchange chromatography (DEAE) resins (Lipinska, et al., 1974, Hasegawa and Sasaki, 1990, Siebenlist, et al., 1996). When these sub-populations are isolated, they do not differ significantly in their biochemical properties (Fibrinopeptide release by Thrombin, % clottability, cross-linking by FXIII). However, they do differ significantly in the structure of the fibrin gels they form and in the physical properties of those gels (Hasegawa and Sasaki, 1990).

Figure 2:
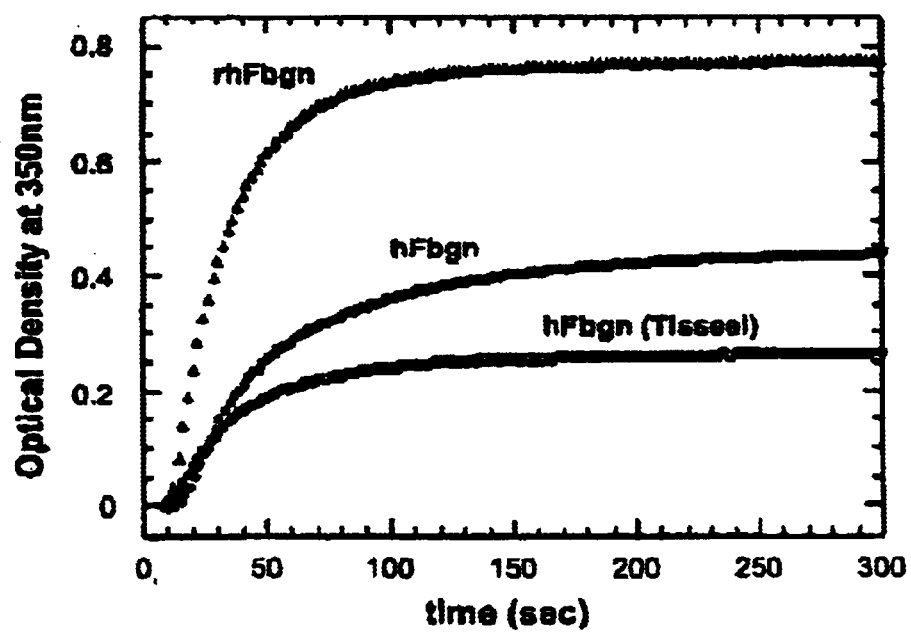
FIG. 2 shows Optical Density profiles monitoring the gelation of rhFbgn, and plasma-derived Fbgn (hFbgn) and Fbgn from a commercial FS (TISSEEL®). These plots demonstrate that Fbgn from different sources behaves differently under identical assay conditions. Conditions of the assay TBS (20 mM Tris-HCl, pH7.4, 120 mM NaCl), 0.2 mg/ml Fbgn, 0.5 U/ml rhThrombin, and 2.7 µg rhFXIII/mg rhFbgn added to the rhFbgn to approximately normalise FXIII levels).

A significant consequence of the inherent heterogeneity of Fbgn is that there is no "standard Fbgn" to which to compare the properties of rhFbgn. The lack of a standard is not noticeable when biochemical or enzymatic assays are compared. All "quality" Fbgn preparations interact with thrombin and FXIII in a similar manner and are >95% clottable. However, it is the physical or "functional" properties of the FS obtained by mixing the Fbgn with Thrombin and FXIII that can vary significantly, depending on the source of the Fbgn. As an example of the magnitude of the variation that can be observed from different sources of "quality" Fbgn under otherwise identical conditions, the clotting curves of three different Fbgn samples is shown in FIG. 2. (The interpretation of these curves is discussed below.)

It is neither practical or necessary to purify rhFbgn to homogeneity to develop a functional rhFS with consistent properties. What is necessary is to have functional assays to characterise the rhFS that is being prepared using the rhFbgn produced by a given process. With these assays, the batch-to-batch consistency of the rhFbgn itself can be evaluated, and the specifications of the final product, rhFS, can be set.

The principles behind the in vitro assays that have been developed to characterise the functional properties of rhFS will now be described. Detailed protocols are included in the examples.

Figure 3:
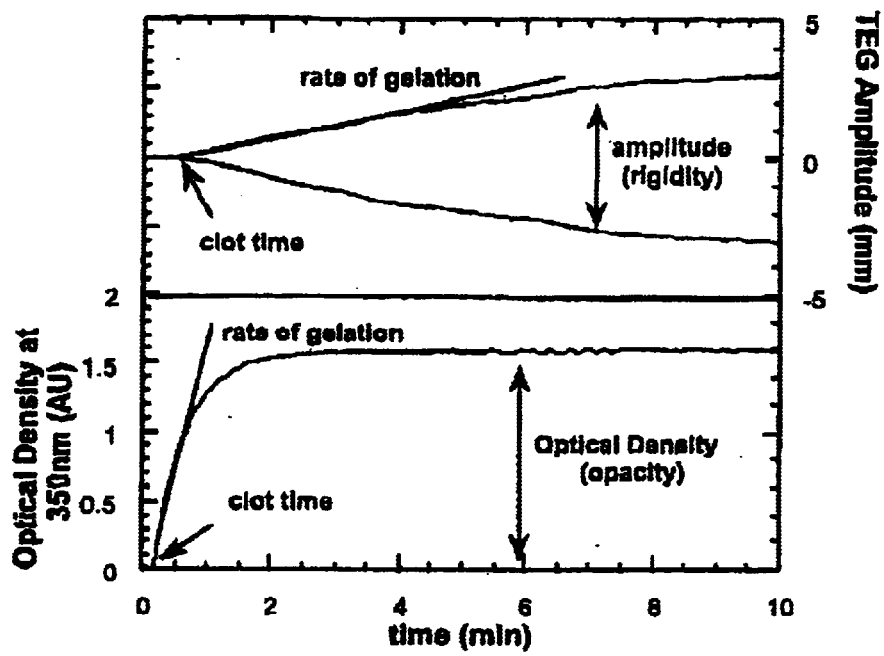
FIG. 3 shows measurements used to characterise rhFS using mechanical (Thromboelastography) and optical (UV-Vis) and measurements. Both techniques yield information on the rate of gelation and the final properties of the rhFS, and can be used to assess the effect of protein formulation and buffer components on the properties of recombinant fibrin sealant. Typically, optical measurements detect gelation earlier than mechanical measurements. Conditions of the assay: 20 mM Tris-HCl, pH7.4, 250 mM NaCl, 5% sucrose, 20 mM CaCl$_2$, 3.0 mg/ml rhFbgn, 1.0 U/ml rhThrombin, 3 µg rhFXIII/mg rhFbgn, 37° C. The optical measurements were taken using a 1 mm path length cuvette.

Macroscopically, rhFS appears as a transparent to opaque, white, rubbery gel. Microscopically, rhFS appears as a meshwork or matrix of fibrin fibres similar to that found in blood clots (FIG. 3). This matrix is thought to provide a provisional scaffold for wound healing (Clark, et al., 1982). Perturbations in the structure of the fibrin matrix are known to have significant effects on the mechanical and optical properties of rhFS. (In fact, many of these same properties were originally used to elucidate the biochemical processes accompanying blood coagulation.) the fibrin gel structure can have profound effects on biological events (Redl and Schlag, 1986).

A complete description of the gel structure of rhFS would include the thickness of the fibrin fibres, the spacing of branch points, the distribution of pore sizes, rigidity, strength, etc. In practice, microscopy cannot be performed on every sample, and physical techniques are commonly used to characterise the functional properties of rhFS. Several of the techniques were originally developed to study blood coagulation and can only be used at rhFbgn concentrations similar to those found in blood (2.5 to 3.0 mg/ml), approximately 10-fold lower than those found in rhFS. However, related techniques can be used to verify that the behaviour of rhFS at low rhFbgn concentration extrapolates to "full-strength" rhFS. One disadvantage of all of the assays performed in vitro is that they use rhThrombin concentrations below those used for haemostatic applications in vivo. Gelation times of 10 sec to 30 minutes, rather than fractions of a second, are necessary to allow time for the rhFS to be placed in the instrument and measurements to be recorded in vitro.

Many of the functional properties of rhFS do extrapolate from low rhFbgn concentrations to high rhFbgn concentrations. Therefore, in order to conserve rhFbgn, most of the initial experiments were performed using rhFbgn concentrations from 2.5–3.0 mg/ml. These experiments were designed to evaluate the effects of formulation buffer and rhFXIII concentration on the properties of rhFS. Three assays formed the basis for this screening: compaction, thromboelastography, and optical density measurements.

Compaction is used to quantify the resistance of the rhFS to syneresis (compression with the resulting squeezing out of fluid). Easily synerised gels compress and lose their fluid easily, whereas less easily synerised gels retain their shape. In practice, the properties of FS can vary between the two extremes. In compaction experiments, the volume of a rhFS sample is measured before and after it has been centrifuged at a specified force for a specified time in a tube to which it does not stick. The greater the resistance to syneresis, the more of the original volume is retained by the sample.

Thromboelastography (TEG) is used to quantify the time dependent change in elastic properties of the rhFS as it gels. In the TEG, the sample is placed inside a cup that is rotated slightly in an oscillatory manner. In the centre of the cup, but not touching the cup directly, is a pin attached to a strain gauge. If there is only a liquid between the cup and pin, no signal is generated. However, when rhFS is placed in the cup, a steadily increasing signal is generated as the rhFS transforms from a liquid to a gel, increases in stiffness, and transmits more of the motion of the cup to the pin. Information derived from a TEG plot include the clot time at which the sample first exhibits solid-like behaviour, the slope of the stiffness vs. time plot as a measure of the rate of gel structure maturation, and the final stiffness of the gel taken at 30 min. or after the signal no longer increases (FIG. 3).

Several other assays measuring the "strength" and degradation rate of FS are extremely useful for the in vitro characterisation of the functional properties of rhFS at high rhFbgn concentrations (25–30 mg/ml final). The "strength" of rhFS encompasses several properties that can be measured independently: the stiffness or rigidity of the rhFS, the ultimate force required to rupture the rhFS, either in tension or shear, and the force of adhesion between the rhFS and the material it has been applied to (adherand). Generally, rhFS prepared with high concentrations or rhFbgn are too opaque for optical measurements to be useful. Three assays form the basis for our in vitro studies of rhFS at high rhFbgn concentration: parallel plate rheometry, tensile adhesion testing, and fibrinolysis rate measurements.

Parallel plate rheometry can be used in a similar manner to TEG, but over a much wider range of operating parameters and rhFS concentrations. The rheometer measures the viscoelastic properties of a gel sandwiched between a fixed circular plate and an oscillating circular plate. The spacing between the plates, rate of rotation of the moving plate, and the magnitude of the oscillatory motion can be varied independently. The amount of distortion (% strain) and the force required to cause that distortion (stress) are the principal measurements that are recorded. The slope of the stress vs. strain curve is the elastic modulus (G') of the gel, a measure of its stiffness. The stiffer and more rigid the gel, the higher the elastic modulus. A related term, the loss modulus (G"), that described the viscous behaviour of the gel, can also be measured. Just as with TEG, time-dependent measurements can be recorded. These are typically taken at very small levels of deformation (% strain), so that the fibrin gel structure is not damaged. From these, clot time, rate of gel structure maturation, and maximal elastic modulus can be obtained. Once the rhFS has solidified, a measure of its cohesive shear strength can be obtained by gradually increasing the amount of oscillatory force (stress) applied to the gel until it ruptures.

The "strength" of rhFS can also be measured with tensile measurements. Using tensile measurements, rhFS can be tested as a bulk solid to measure its cohesive strength, or it can be sandwiched between two surfaces (adherands) and pulled apart to measure its strength of adhesion. Adhesive measurements can also be performed in shear (Sierra, 1993, Siedentop, et al., 1988, T Brodneiwizc, personal communication) or peeling geometries. Regardless of the geometry, identifying the failure mode of rhFS is an important part of the assay. We have designed our assay to test a film of rhFS of known thickness, so that we can visually distinguish between cohesive failure of a weak, yet adhesive sealant and adhesive failure at the sealant-adherand interface of an otherwise cohesively strong rhFS. In practice, cohesive failure is observed only at very low fibrinogen concentrations. We have also designed a set of reusable stainless steel jigs to make preparation of samples for tensile adhesion testing quicker and more reproducible. Even so, replicates of 20 or more may be necessary to obtain statistically significant results.

Figure 4:
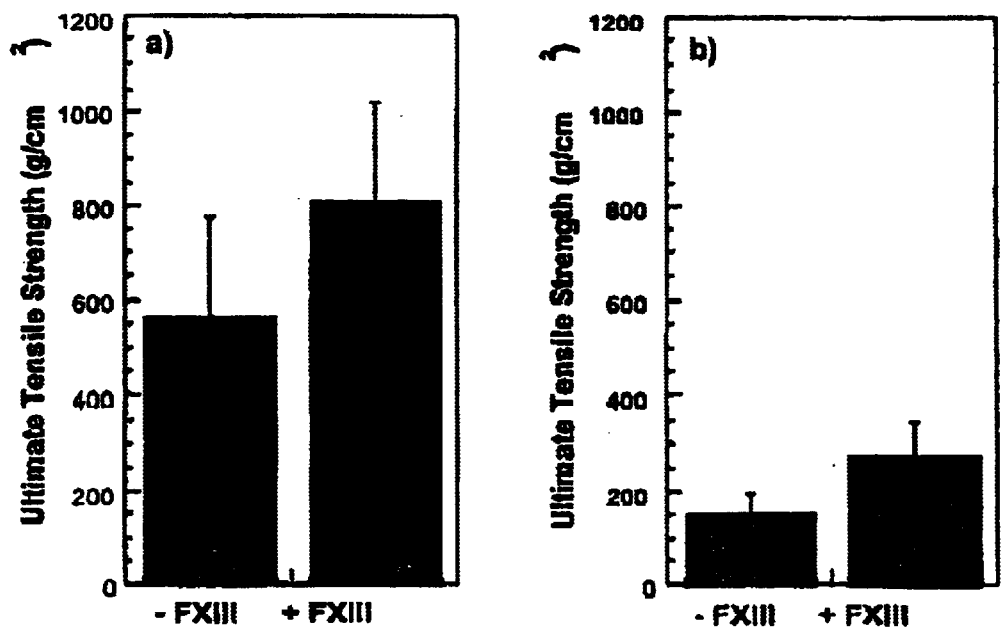
FIG. 4 shows a plot demonstrating the effect of rhFXIII on the tensile adhesive strength of rhFS adhering to Silastic (medical grade silicone rubber) and split calf skin. The adherands were punched into 2 cm diameter discs and epoxied to custom stainless steel jigs. Spacers were used between the top and bottom jigs to create a known thickness of rhFS that could be seen so that failure mode (cohesive vs. adhesive) could be established. The ultimate tensile strength (UTS) is reported as the force at rupture normalised for the surface area of the rhFS. Conditions of the assay: TBS (20 mM Tris-HCl, pH7.4, 120 mM NaCl), 20 mM or 5 mM CaCl$_2$ (Silastic and calf skin, respectively), 30 mg/ml rhFibrinogen, 1.0 U/ml or 0.5 U/ml rhThrombin (Silastic and calf skin, respectively), and 10 µg or 5 µg rhFXIII/mg rhFbgn (Silastic and calf skin, respectively). The samples were incubated at 37° C. for 30 min. and pulled apart at 5.0 mm/min or 2.5 mm/min (Silastic and calf skin, respectively).

The strength of adhesion is determined by the properties of the adherand as well as the rhFS. The importance of this issue is illustrated by the observation that the strength of adhesion or rhFS to a synthetic adherence, such as SILASTIC™ (medical grade silicone rubber), is significantly greater than the adhesive strength to a tissue, such as skin or dura (FIG. 4 and Siedentop, et al., 1995, Park, et al., 1997, Siedentop, et al., 1997). From a practical standpoint, a reproducible adherand would be useful for comparing different preparations of rhFS. However, while a synthetic adherand such as Silastic can be readily prepared, a reproducible tissue adherand cannot. We have evaluated the tensile strength of adhesion of FS to a variety of synthetic adherands (stainless steel, aluminium foil, acetate film, nitrocellulose, Silastic), and a variety of tissues (split pig skin, split calf skin, fresh and frozen full thickness rat skin, and numerous other tissues such as dura, intestine, and tendon that can be prepared as flat sheets.). Additional variables such as humidity are known to significantly affect the results, but are difficult to control reproducibly (G T Rodeheaver, personal communication). In general, these assays are relatively insensitive to small changes in formulation variables unless extremely large numbers of replicate samples are tested.

In spite of the fact that adhesion assays are so difficult to perform, adhesive "strength" is a functional property that holds great perceived significance. However, there are no studies in the literature correlating the in vitro "strength" of different FS preparations with their in vivo efficacy. Regardless, an adhesion assay involving living animals is still commonly used as a QC assay for FS. (This attests to the difficulty of finding reproducible, biologically relevant adherands for adhesion assays.) In one configuration, a full thickness skin patch of a fixed size is excised from the back of an anaesthetised mouse or rat, then glued back with FS. After a predetermined incubation time, the skin patch is pulled off while the force required to remove it is recorded by a materials testing instrument (Kjaergard and Weis-Fogh, 1994). We have observed similar results when comparing different formulations FS with tensile assays using anaesthetised rats, and assays using split pig skin (S Busby and M Buddle, data not shown).

Ideally, as a surgical site to which FS is applied heals, the newly formed tissue in the wound will develop mechanical strength at a rate close to that at which the FS degrades and loses its mechanical strength. As with adhesion, testing, the properties of the surrounding tissue, in addition to those of the rhFS itself, will determine the in vivo degradation rate. Unfortunately, the minimum strength that the healing wound must maintain is not well established, and will vary depending on the location of the wound, and type of surrounding tissue. However, just as "strength" is a functional property that holds great perceived significance, so is the degradation rate.

While FS can be degraded in vivo via proteolytic and cellular processes, the degradation in vitro is most easily determined for proteolysis. If plasma-derived Fbgn is used to prepare the FS, and still contains plasminogen, then proteolysis (fibrinolysis) can be initiated by the addition of plasminogen activators, such as streptokinase or tPA. If the FS is free of endogenous plasminogen, as is the case with rhFS, then fibrinolysis must be initiated by the addition of plasmin, plasminogen +activator, or other proteases such as leucocyte elastase (Edwards, et al., 1993). For our studies, we have chosen plasmin. Fibrinolysis assays can be performed by either adding the protease to the FS prior to polymerisation, or by placing the already polymerised FS into a solution containing protease. Since rhFS is not normally formulated to contain proteases, the later assay format was adopted. When observed visually, rhFS degrades at the solution/sealant interface, rather than homogeneously throughout its volume. Since the bulk of the rhFS maintains its structural integrity until the very last stages of lysis, the unlysed rhFS can easily be separated from the solution containing the protease and soluble Fbn fragments. This provides the basis for a simple assay in which the concentration of soluble Fbn fragments is measured at timed intervals to determine the rate of fibrinolysis. The concentration of fragments can be measured using UV-Vis spectrophotometry (Siebenlist and Mosesson, 1994). We have performed fibrinolysis experiments using rhFS that was allowed to gel followed by incubation overnight at 37° C. The rhFS samples were then floated in a solution of human plasmin at 37° C. At timed intervals, samples of the solution were taken, and the concentration of soluble fragments was measured based on its absorbance at 280 nm. After the rhFS was entirely dissolved (lysed), the absorbance was again measured to obtain the value for 100% lysis. The time points were then plotted as % lysis vs. time to obtain the rate of fibrinolysis.

Most of the experiments herein were performed in a Tris-HCl/NaCl (TBS) buffer system. Other buffer systems may also be suitable for this purpose. While the specific behaviour of the rhFS may change somewhat depending on the final formulation buffer, the general trends described herein should hold.

Pilot experiments indicated that rhFS formulated in TBS tended to synerise more readily than FS made with plasma-derived Fbgn, its endogenous FXIII, and rhThrombin. In addition, although the rate of gelation was fast, the rhFS was not very stiff when characterised by TEG, and was very opaque when characterised by OD measurements. In concert, these properties indicated that the gel structure was extremely coarse, and had thick fibres and large pores.

While there was no biology-driven justification to modify the gel structure of the rhFS, a gel structure that was intermediate between the extremes of coarse and fine for our initial evaluation was determined. Gel structure can be modulated by many different formulation variables: Fbgn concentration, FXIII concentration, Thrombin concentration, pH, ionic strength, and additives such as sugars.

Figure 5:
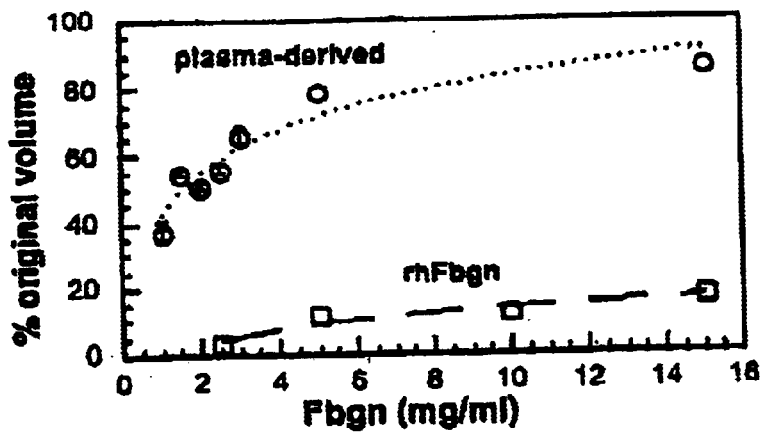
FIG. 5 is a plot showing the effects of Fbgn concentration on the compaction behaviour of FS. The behaviour of FS using plasma-derived Fbgn and rhFbgn are compared. The data are plotted as the % or the original volume occupied by the sealant after centrifugation. Conditions of the assay: TBS (20 mM Tris-HCl, pH7.4, 120 mM NaCl), 5 mM CaCl$_2$, 2.5 to 15 mg/ml Fbgn, 0.5 U/ml rhThrombin, and 10 µg/ml rhFXIII (added to the rhFbgn only). The samples were incubated at 37° C. for 1 hr prior to centrifugation for 45 sec at 8000×g.

With plasma-derived Fbgn, FS gels compact readily at low Fbgn concentration, but resist compaction at Fbgn concentrations above ~5 mg/ml Fbgn. The effect of rhFbgn concentration on compaction was investigated first to see whether or not rhFbgn concentration alone could be used to produce rhFS with desirable functional properties. In stark contrast to the behaviour of FS prepared from plasma-derived Fbgn, the compaction behaviour did not improve significantly at high rhFbgn concentrations (FIG. 5).

The addition of rhFXIII to rhFS also had little effect on compaction. This is discussed in more detail in the next section. Increasing thrombin concentration can produce a finer gel structure. However, since rhFS gels rapidly (10–20 sec), even at low rhThrombin (1 U/ml) concentrations, it was not feasible to increase the rhThrombin concentration significantly.

Figure 6:
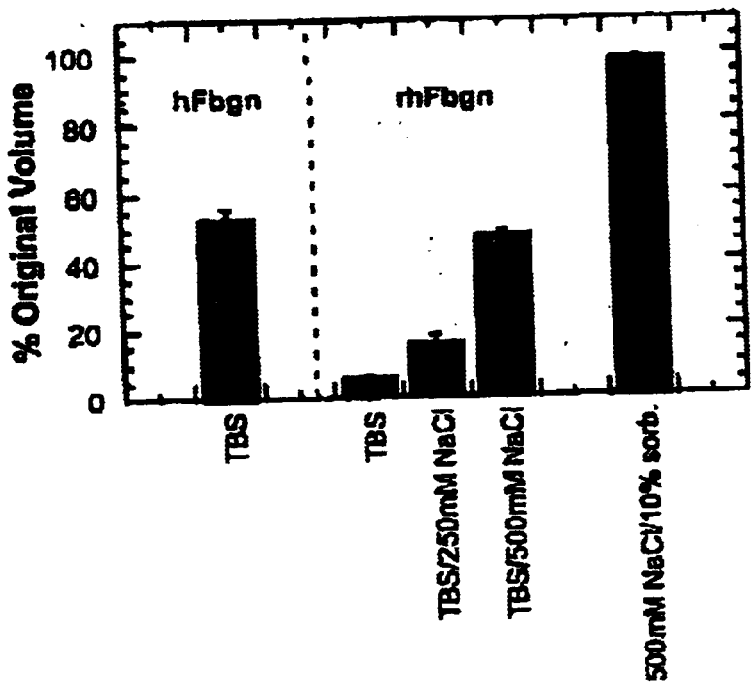
FIG. 6 is a plot demonstrating the effects of added salt (increasing ionic strength) and added sorbitol on the compaction behaviour or rhFS. The behaviour of FS using plasma-derived human Fbgn (hFbgn) is shown as a reference. The data are plotted as the % of original volume occupied by the sealant after centrifugation. Conditions of the assay: TBS (20 mM Tris-HCl, pH7.4, 120 mM NaCl), 5 mM CaCl$_2$, 2.5 to 15 mg/ml Fbgn, 0.5 U/ml rhThrombin, and 67 µg rhFXIII/mg rhFbgn (added to the rhFbgn only). The samples were incubated at 37° C. for 1 hr prior to centrifugation for 45 sec at 8000×g.

The effects of ionic strength (added NaCl) and sugars (added sucrose or soibitol) on the properties of rhFS were examined. Both added NaCl and sugar decreased compaction in a synergistic manner (FIG. 6). Concomitantly, stiffness as measured by TEG increased, and opacity as measured by OD, decreased. Additionally, both added NaCl and sugar tended to increase clot times. When rhThrombin concentration was increased to compensate for the increased clot time, additional increases in stiffness and decreases in OD were observed. In concert, this behaviour indicated that the rhFS was shifting towards a finer gel structure.

Figure 7:
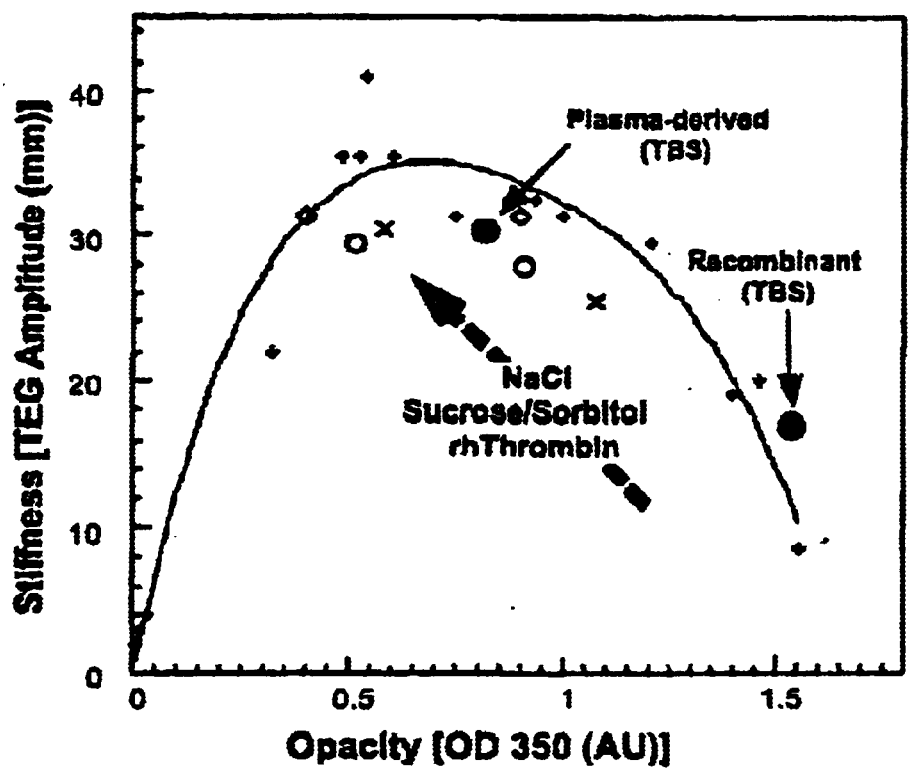
FIG. 7 is a diagram illustrating the relationship between stiffness, as measured by TEG, and opacity of rhFS over a wide range of buffer conditions and rhThrombin concentrations. The properties of recombinant and plasma-derived FS in TBS, and the general effects of formulation changes are indicated on the diagram. At the limit of low opacity (fine gel), the gel becomes friable, and the mechanical behaviour of the gel degrades rapidly. Conditions of the assay: 20 mM Tris-HCl, pH7.4, 120 to 500 mM NaCl, 0 to 9% sucrose, 20 mM CaCl$_2$, 3.0 mg/ml rhFibrinogen, 1.0–1.4 U/ml rhThrombin, 3 µg rhFXIII/mg rhFbgn, 37° C. The optical measurements were taken using a 1 mm path length cuvette.

When data from a large number of experiments using varying NaCl, sugar (sucrose), and rhThrombin concentrations were combined, a general picture of the effect of these formulation variables on gel structure emerged (FIG. 7). As NaCl, sucrose, or rhThrombin were increased, the stiffness and resistance to compaction increased as the opacity decreased. However, at the extreme range of find, transparent gels, the stiffness dropped off precipitously and friable, easily damaged, though incompressible, gels resulted.

Also, but not readily apparent from FIG. 7, the concentration-dependent effects of salt and sugar were non-linear. There was a gradual modification of properties until a sharp transition was observed at some critical value. This type of non-linear behaviour was observed for many variables that effect gel structure (Shulman and Ferry, 1949).

As a result of these experiments, a formulation buffer of 4.5% sucrose in TBS was chosen for further work. [Note that these buffer components were chosen only to illustrate the potential effects of formulation variables on gel structure. They are not intended to represent an optimised formulation buffer, and TBS+4.5% sucrose may or may not be a recommended formulation buffer for a final product.] The TBS+ 4.5% sucrose buffer produced rhFS with a gel structure that was neither extremely coarse, nor extremely fine, and behaved in a similar manner to that of FS prepared from plasma-derived Fbgn.

Figure 8:
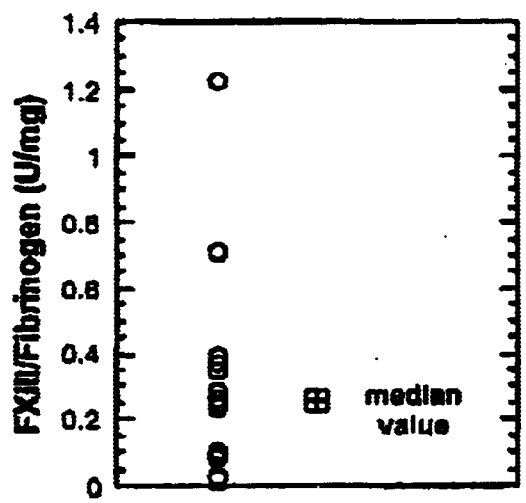
FIG. 8 illustrates the reported range of FXIII concentrations in commercial FS (Radosevich, et al., 1997, Jackson, et al., 1996). The rhFXIII concentration has been plotted as the ration of FXIII to Fbgn (U/mg). For comparison with the data in the rest of this report 1 Unit=10 µg FXIII (Yorifuji, et al., 1988). Assuming 1 U/ml FXIII and 2.5 mg/ml Fbgn, the ratio of FXIII to Fbgn in normal human plasma is approximately 0.4 U/mg.

When FS are prepared from Fbgn derived from pooled human plasma, FXIII is normally present as a contaminant that co-purifies with the Fbgn. As such, the concentration of FXIII is reported, but is not actively controlled. With few exceptions, FS derived from pooled human blood contains FXIII in levels close to or below the levels found in blood (FIG. 8). While FXIII is generally thought to be a necessary component of FS (especially in Europe, where some plasma-derived FS have FXIII concentrates added back if FXIII was depleted during the purification of the Fbgn), this assumption is still controversial, especially in the US. Since the components of rhFS are highly purified, rhFS will not contain rhFXIII unless it is deliberately added. For regulatory purposes, this addition, and the concentration of rhFXIII in the final product, must be justified experimentally. This justification is the purpose of the experiments described in the following paragraphs.

Figure 9:
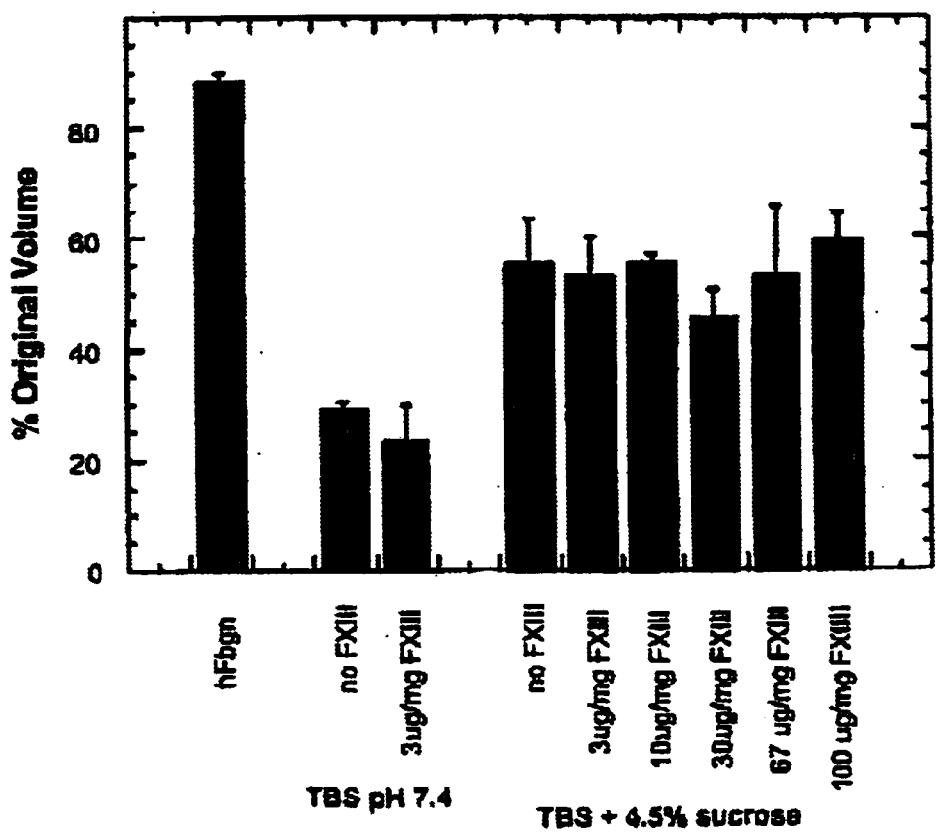
FIG. 9 is a plot demonstrating the effects of added rhFXIII and added sucrose on the compaction behaviour of rhPS. The behaviour of FS using plasma-derived Fbgn (hFbgn) is given as a reference. The data are plotted as the % of the original volume occupied by the sealant after centrifugation. The rhFXIII concentration is given as the ratio of rhFXIII to rtiFibrinogen ($\mu$g/mg). Conditions of the assay: TBS (20 mM Tris-HCl, pH7.4, 120 mM CaCl$_2$, 2.5 mg/ml rhFbgn, 0.5 U/ml rhThrombin. The samples were incubated at 37° C. for 1 hr, prior to centrifugation for 45 sec at 8000×g.

As mentioned previously, prior to evaluating the effect of formulation buffer on the properties of rhFS, the addition of rhFXIII was evaluated as a means to modify gel structure and increase resistance to compaction. The addition of rhFXIII to rhFS had little effect on compaction. After the TBS+4.5% sucrose buffer was chosen for further experiments, the effect of rhFXIII was re-evaluated again. Again, the addition of rhFXIII to rhFS had little additional effect on compaction beyond that obtained by the addition of sucrose (FIG. 9). This would suggest that rhFXIII has little effect on the porosity of the gel structure. Our observations are contrary to those recently reported by Nair et al (Nair and Shats, 1997), that demonstrated an increased resistance to compaction as a result of increased cross-linking by FXIII.

Figure 10:
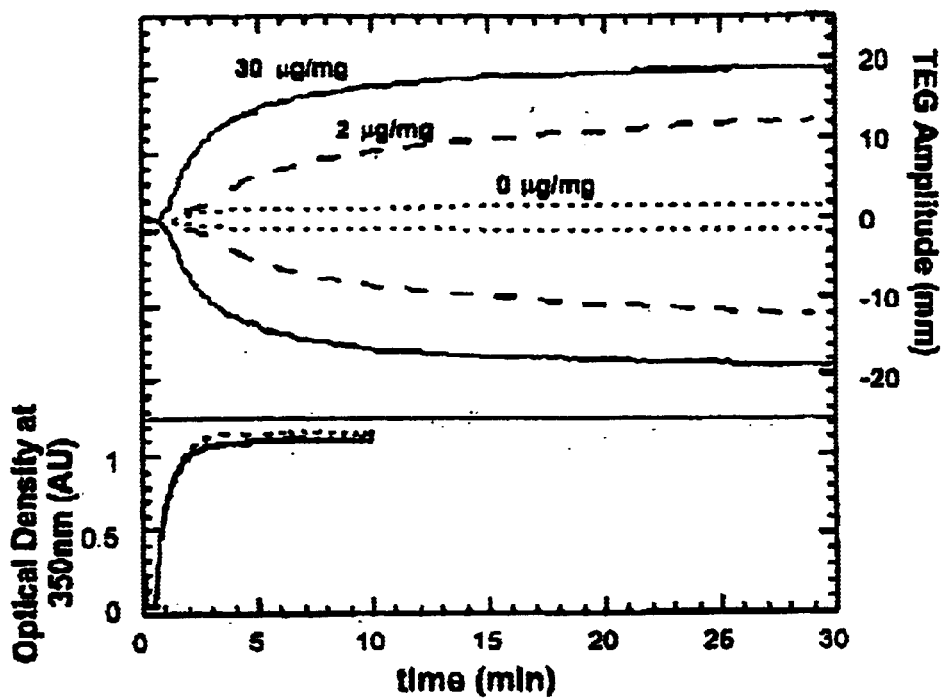
FIG. 10 is a plot demonstrating the concentration-dependent effect of rhFXIII on the development of the mechanical and optical properties or rhFS as measured by Thromboelastography (TEG) and UV-Vis spectroscopy. Conditions of the assay: TBS (20 mM Tris-HCl, pH7.4, 120 mM NaCl), 4.5% sucrose, 20 mM CaCl$_2$, 3.0 mg/ml rhFbgn, 1.0 U/ml rhThrombin, 37° C. The rhFXIII concentration is given as the ratio of rhFXIII to rhFbgn ($\mu$g/mg). The optical measurements were taken using a 1 mm path length cuvette.

Added rhFXIII also had little effect on OD, suggesting that rhFXIII does not significantly modify the fibre size or pore structure of the gel. However, rhFXIII did have a significant effect on the rigidity of rhFS, as measured by TEG (FIG. 10).

Figure 11:
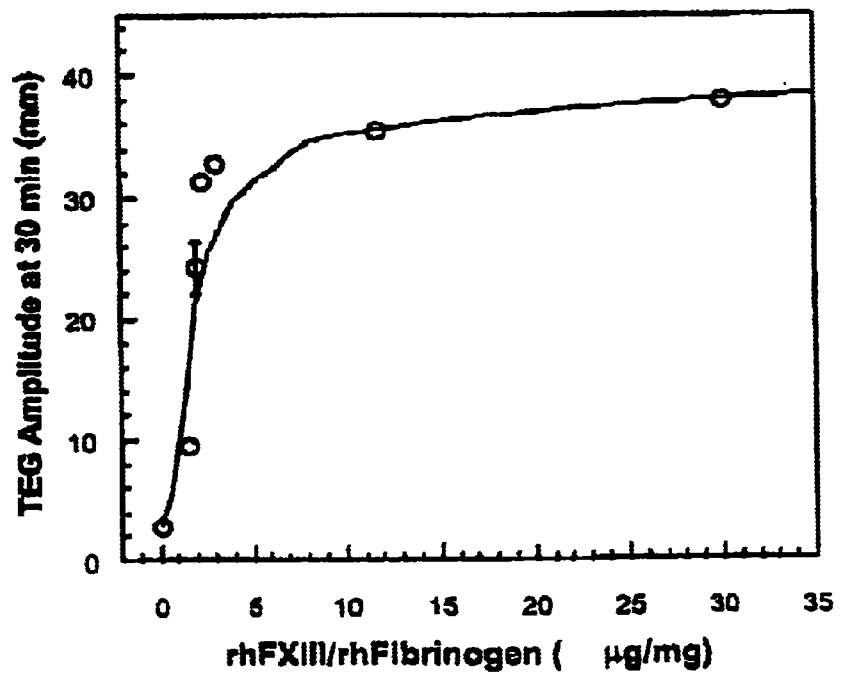
FIG. 11 is a plot demonstrating the concentration-dependent effect of rhFXIII on the mechanical properties of rhFS as measured by TEG. Conditions of the assay: TBS (20 mM Tris-HCl, pH7.4, 120 mM NaCl), 4.5% sucrose, 20 mM CaCl$_2$, 3.0 mg/ml rhFbgn, 1.0 U/ml rhThrombin, 37° C. The rhFXIII concentration is given as the ratio of rhFXIII to rhFbgn ($\mu$g/mg). The TEG amplitude (mm) was measured 30 minutes after mixing.

When plotted as a dose-response curve, the effect of rhFXIII on the TEG amplitude is non-linear, and exhibits a very steep dose-response at low rhFXIII concentrations, and a more shallow dose-response at higher rhFXIII concentration (FIG. 11). The change in behaviour occurs at 3–4 $\mu$g rhFXIII per mg rhFbgn. This level is approximately that found endogenously in plasma (and in existing FS). Consequently, the role of FXIII in determining the properties of FS would be overlooked in experiments performed using plasma-derived Fbgn, unless it had been specifically depleted of contaminating FXIII (i.e. adding supraphysiological amounts of FXIII results in little change in the TEG amplitude).

Figure 12:
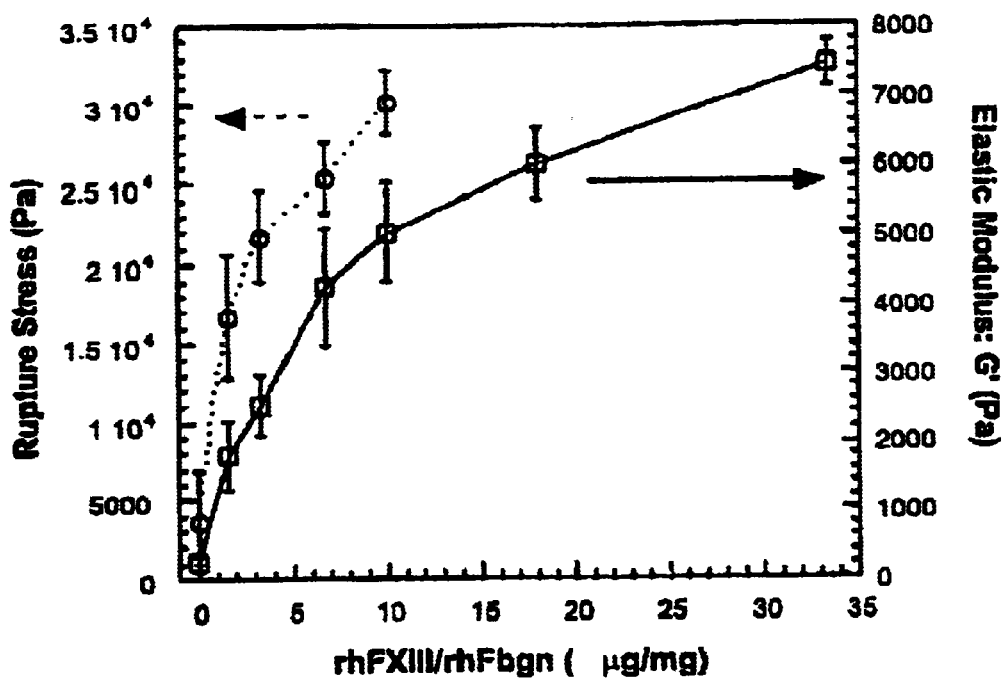
FIG. 12 is a plot demonstrating the concentration-dependent effect of rhFXIII on the mechanical properties of rhFS as measured by parallel plate rheometry. Elastic modulus was measured with small deformation of the sample (1 Hx oscillations at 1% strain) for 30 minutes, followed by oscillations of increasing amplitude until the sample ruptured. Conditions of the assay: TBS (20 mM Tris-HCl, pH7.4, 120 mM NaCl), 4.5% sucrose, 20 mM CaCl$_2$, 23 mg/ml rhFbgn, 1.0 U/ml rhThrombin, 37° C. The rhFXIII concentration is given as the ratio of rhFXIII to rhFbgn ($\mu$g/mg). The data are plotted as the mean and standard deviation of 5 replicates.

Rheometry confirmed that the rhFXIII-induced increase in stiffness observed using TEG extrapolates to high rhFbgn concentration rhFS. With the rheometer, the actual elastic modulus (G'), rather than a signal amplitude, was measured as a function of the rhFXIII concentration. The dose-response curve is non-linear, as was observed with the TEG. In addition to the increase in modulus, the shear rupture strength of the rhFS is increased dramatically by the addition of rhFXIII. The highest value on the rupture stress vs. rhFXIII/rhFbgn ratio curve (FIG. 12) represents the high stress limit of the rheometer, so the dose-dependent effect of rhFXIII on the rupture stress of rhFS above 10 $\mu$g rhFXIII/mg rhFbgn was not determined. While the significance of the elastic modulus to the in vivo function of rhFS is difficult to discern, the increase in rupture stress afforded by the addition of rhFXIII should be relevant to in vivo applications, such as skin graft fixation.

When the rhFS ruptured, rhFS was left in patches on both plates of the rheometer, suggesting that the rhFS failed cohesively. The increase in rupture strength of the rhFS accompanying the addition of rhFXIII is consistent with reports in the literature demonstrating that crosslinking by FXIII significantly increases the cohesive tensile strength of FS (Marx and Blankenfeld, 1993, Nowotny, et al., 1982).

Figure 13:
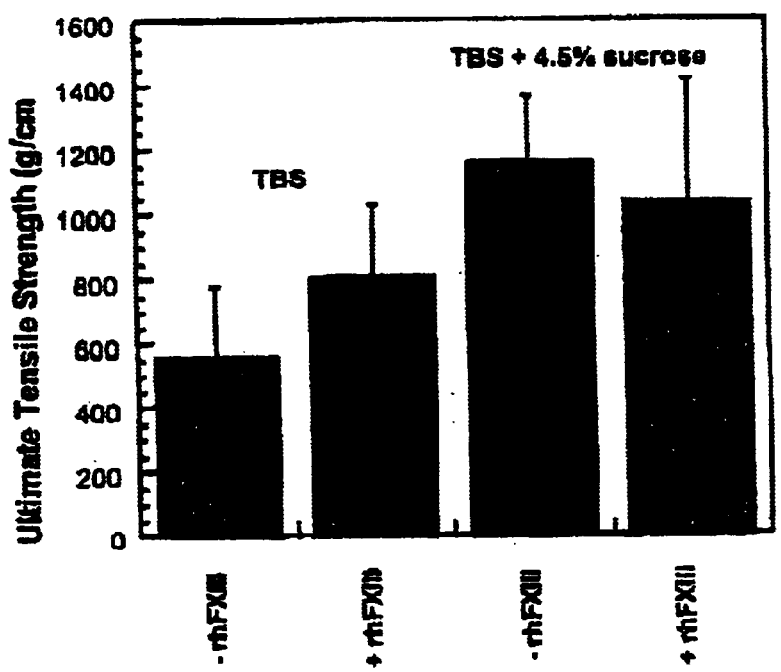
FIG. 13 is a plot demonstrating the effect of rhFXIII and 4.5% sucrose, both alone and in conjunction, on the tensile adhesive strength of rhFS adhering to silastic (medical grade silicone rubber). The ultimate strength (UTS) is reported as the force at rupture normalised for the surface area of the rhFS. Conditions of the assay: TBS (20 mM Tris-HCl, pH7.4, 120 mM NaCl), 20 mM, 30 mg/ml rhFbgn, 1.0 U/ml rhThrombin, and 10 $\mu$g rhFXIII/mg rhFbgn. The samples were incubated at 37° C. for 30 minutes and pulled apart at 50 mm/min.

While the beneficial effect of FXIII on the cohesive strength of FS is generally accepted, the effect of FXIII on adhesive strength is controversial (G Marx, personal communication). Our studies shed some light on this controversy. When rhFS was formulated in TBS, a formulation that has been demonstrated to generate very coarse gel structure, a significant increase in tensile adhesion strength was observed using silastic as an adherand (FIG. 13). Similar results were obtained using acetate and split bovine skin as adherands. However, when sucrose was added to the formulation, the tensile adhesive strength (to silastic) increased even in the absence of rhFXIII, and no added effect of rhFXIII was observed (FIG. 13). These observations suggest that tensile adhesive strength measurements, especially to synthetic adherands, are very sensitive to gel structure. We would predict that the choice of formulation buffer could either amplify or diminish the observed effect of rhFXIII on the tensile adhesive strength of rhFS.

The effect of rhFXIII on the degradation rate of rhFS was also evaluated. As with "strength", degradation rate is a functional property that holds great perceived significance. This is in spite of the fact that the properties of the surrounding tissue, in addition to those of the rhFS itself, wili determine the degradation rate, and that there are no studies correlating degradation rate with in vivo efficacy. Previous studies by Edwards et al. and by Siebenlist and Mosesson have demonstrated that FXIII decreases the rate of fibrinolysis in a dose-dependent manner (Edwards, et al., 1993, Siebenlist and Mosesson, 1994).

Figure 14:
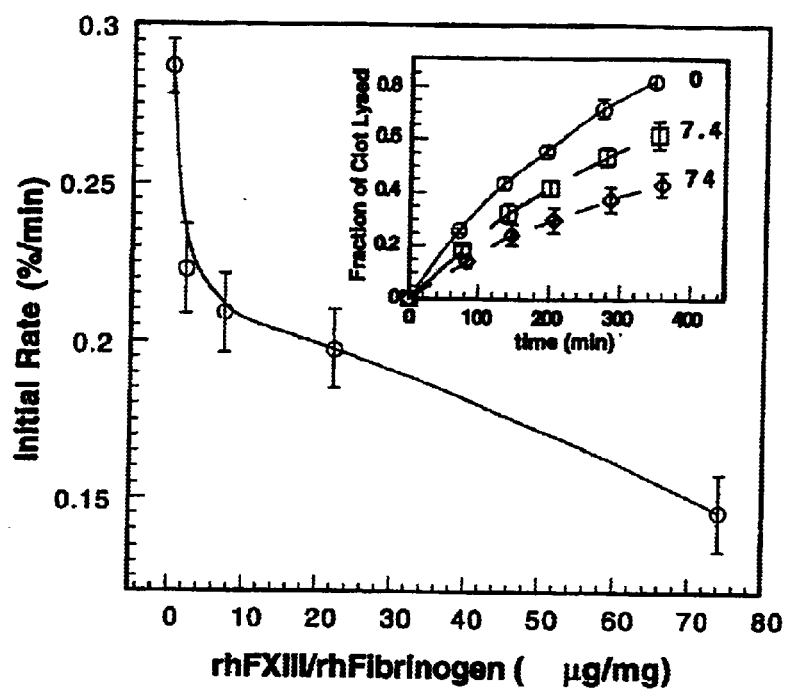
FIG. 14 is a plot demonstrating the concentration-dependent effect of rhFXIII on the rate of degradation of rhFS by plasmin. The rhFXIII concentration is plotted as the ratio of rhFXIII to rhFibrinogen ($\mu$g/mg). The rate (%/min.) is the initial rate determined from the linear portion of the plots of fraction lysed vs. time (see inset). Conditions of the assay: TBS (20 mM Tris-HCl, pH7.4, 120 mM NaCl), 4.5% sucrose, 20 mM CaCl$_2$, 20 mg/ml rhFibrinogen, 3.0 U/ml rhThrombin, and 0 to 1.48 mg/ml rhFXIII. The samples were incubated at 37° C. for 16 hr, and lysed with a solution of 8 $\mu$g/ml hPlasmin in 50 mM Tris-HCl, pH8.6, 10 mM CaCl$_2$.

Initial experiments determined that a plasmin concentration of 8 $\mu$g/ml (~0.2 cu/ml) lysed most rhFS samples in 4 to 6 hours. The same plasmin concentration was used to lyse rhFS containing increasing concentrations of rhFXIII. The largest effect of rhFXIII was seen between 0 and 3 $\mu$g rhFXIII per mg rhFbgn (approximately physiological level). However, supraphysiological concentrations from 3 to 74 $\mu$g rhFXIII per mg rhFbgn continued to decrease the rate of fibrinolysis in a dose-dependent manner (FIG. 14). This dose dependent behaviour is similar to that reported by Siebenlist and Mosesson using non-recombinant reagents, but similar lysis conditions. Recently, Siebenlist and Mosesson have refined their studies and demonstrated that, in addition to the concentration of FXIII, the initial structure of the fibrin gel determines the number of multimeric (distinct from dimeric) cross-links involving the gamma-chain of fibrinogen, and that these multimeric cross-links determine the rate of fibrinolysis of the gel (Siebenlist and Mosesson, 1994). These results impart significance to our ability to modulate gel structure by modifying the formulation buffer. We would predict that the choice of formulation buffer could either increase or decrease the effect of rhFXIII on the rate of fibrinolysis of rhFS.

Much of the data supporting the need for anti-fibrinolytic agents, such as aprotinin and EACA, and FXIII is FS is based on in vitro measurements of "strength" and degradation rate. This is in spite of the fact that the failure modes of FS in vivo are difficult to determine, and are not generally reported. While a direct correlation between in vitro properties and in vivo efficacy may be established, there are no studies in the literature which unambiguously make this correlation. Therefore, in addition to in vitro assays, some form of in vivo assay is necessary to verify the function of rhFS in a surgical application.

Fibrin Sealants (FS) have been in clinical use for fifty years. Starting as a battlefield haemostatic agent, FS have found a niche in a myriad of clinical applications from nerve anastomosis to use as a matrix for bone regeneration. The use of FS in medicine has been championed by a few individuals around the world who recognise the potential of this type of product. While FS has been approved for use in Europe, Canada and Japan, it has yet to find itself in the mainstream of medicine. Perhaps the fact that it is a plasma derived product, and has no consistent formulation, has clouded the view of clinicians regarding its potential.

As might be imagined, along with the many clinical uses of FS has come a host of animal studies. Many of these models appear to have evolved from individual surgeons' interest and their clinical focus. In general, these models have not been exported to other laboratories.

Outlined below are a few of the clinical applications for FS and the animal models that have been used to test them. The FS used in all these models has been plasma derived. Little or no information on FS formulation is reported with these products beyond the inclusion of proteolytic inhibitors and varying the thrombin level. The ability to precisely manipulate rhFbgn, rhFXIII and rhThrombin concentrations along with buffer additives offers the exciting opportunity to consistently modulate the properties or rhFS. Each clinical application of rhFS may benefit from a customised formulation.

Orthopaedics

FS has been effective as a delivery device for osteogenic factors, bone powder, coral granules and autologous cancellous bone in bone repair models. A FS human trial was successful for meniscal repair. However, it has not proven to be a replacement for sutures in meniscal repair in animals. Its use as a drug delivery matrix has promise in this application. The results of several published studies are summarised below:

1. FS can act as a carrier and scaffold in bone repair. A rabbit bilateral cranioplasty model showed accelerated osteogenesis with FS combined with TGF-beta and coral (madreporic calcium carbonate) (Arnaud et al., 1994).
2. A combination of demineralized bone powder and FS allowed bone formation to occur, improved handling of bone powder, and facilitated shaping of implants in a rat calvarial defect model. The concentration of Fbgn in the FS was 30 mg/ml (Lasa et al., 1995).
3. The addition of FS to coral granules promoted bone repair in a rabbit femoral defect model. Two commercial FS were compared, one of which contained PDGF and TGF-beta. Both products showed enhanced bone formation at 1 month, whereas at 2 months only the FS enriched with growth factors showed significant enhancement of bone repair (Kania et al., 1998).
4. Endothelial cell growth factor combined with FS showed improved healing in meniscal repair after 1 week. No difference was seen at 12 weeks (Nabeshima et al., 1995).

Remodelling of heterologous or homologous bone grafts would benefit from an rhFS with high adhesive strength and tensile strength, while elasticity may not be as important. For tendon surgery, however, a tailored rhFS may benefit from a high degree of both elasticity and tensile strength, which may be achieved by having a high thrombin concentration and optimal rhFXIII to ensure adequate rigidity but allowing movement. The present invention allows such diverse requirements to be precisely catered for.

Skin Grafting

Cultured epidermal sheets are an important tool for skin restoration following serious burns. FS enhances graft take, especially in areas difficult to engraft, and improves mechanical stability. The results of several published studies are summarised below:

1. FS was applied prior to the deposition of cultured epidermal sheets to a muscular bed in nude mice. Enhanced engraftment occurred (Xu et al., 1996).
2. A study done essentially as above showed that FS enhanced graft take and improved the mechanical stability of epidermal sheets. In addition, histologic examination showed no interference by FS to the sequence of basement membrane formation (Auger et al., 1993).
3. Infection of graft sites are associated with skin graft failure. A rat model showed that FS restores graft adherence to infected sites (Jabs et al., 1992).

Skin grafting may require that clots be formed with small pores, thereby increasing resistance to compaction. High tensile strength and adhesiveness may also be advantages. A sealant of the invention may be tailored with high rhFXIII and rhThrombin concentrations. Alternatively, for some procedures it is desirable for larger pores within the clot to allow infiltration of epithelial cells during tissue regeneration. This could be accomplished with low rhThrombin concentration but high rhFXIII concentration.

Haemostasis

The ability of FS to control bleeding has been tested in numerous models. It has been shown to stop oozing from suture lines, as well as to stop profuse bleeding following severe liver or splenic injury. The results of several published studies are summarised below:

1. FS achieved haemostasis in a canine model of splenic trauma. Lacerations (small and large), wedge resections and stab wounds were all successfully repaired with FS, allowing splenic preservation (Kram et al., 1986).
2. A model developed in New Zealand White rabbits illustrated the effectiveness of FS as a haemostatic agent following partial splenectomy. There was no recurrent bleeding and complete healing occurred over 10 weeks (Kuzu et al., 1992).
3. Severe bleeding was controlled by FS following removal of a section of rat kidney. Haemostasis was achieved in 0.5 min., as compared to 4 min. for the control (Raccuia et al., 1992).
4. FS stopped bleeding in a porcine atrial rupture model as observed for 30 min., indicating the potential of FS in emergency medicine (Kjaergard et al., 1995).
5. A FS haemostatic bandage was used in a porcine model to control bleeding from a femoral artery laceration, illustrating its use as an adjuvant for controlling haemorrhage in the pre-hospital setting (Larson et al., 1995).

In embodiments of the invention particularly tailored for use in haemostasis, little or no rhFXIII may be required, since clot persistence may not be desirable, but a high thrombin content may be an advantage to promote rapid clotting.

Wound Healing

In practice, any clinical use of FS involves wound healing. The use of fibrin sealant has been associated with prevention of adhesions, decreased wound contraction and enhanced skin engraftment. The results of several published studies are summarised below:

1. In a rat skin graft model, FS was shown to inhibit wound contraction of full-thickness defects if applied prior to the graft (Brown et al., 1992)
2. Adhesions were dramatically reduced in a rabbit uterine horn model by FS (De Iaco et al., 1994).
3. Bilateral skin flaps raised over the parotid gland in rabbits glued with FS showed significantly less wound drainage and improved coaptation of skin flaps (Bold et al., 1996).

4. Subcutaneous pockets in the back of rats were implanted with FS. FS was found to be bio-compatible, did not promote an inflammatory response, showed an increase in blood vessels and capillaries and an enhanced extracellular matrix (Romanos and Strub, 1998).
5. Peritoneal adhesions were prevented by FS in a rat model following excision of the parietalmuscular layer, assessed one week after surgery (Lindenberg and Lauritsen, 1984).

Seroma Prevention

The occurrence of seroma following mastectomy, neck resection or any surgery that leaves a raised skin flap is a significant clinical problem. FS has been shown to be an effective agent in preventing seroma formation. The result of several published studies are summarised below:
1. A rat mastectomy model was used to compare the efficacy of a commercial light-activated FS with blood-bank derived FS. Both showed efficacy (Wang et al., 1996). The same group (UVa) has demonstrated the efficacy of autologous FS in a human mastectomy trial (Moore et al., 1997).
2. The rat mastectomy model was used to evaluate the effect of Fbgn and thrombin concentration on the effectiveness of FS in reducing seroma volume. Though not statistically significant, the trend indicated that seroma volumes decreased with both increasing Fbgn and thrombin concentrations. The basic FS showed typical efficacy (Sanders et al., 1996).
3. FS was shown to be effective in a rat model of modified radical neck dissection. 5 days post surgery only 10% of experimental animals presented with seroma, as compared to 85% of controls (Lindsey et al., 1988).
4. The rat mastectomy model was reproduced by a different group to demonstrate the effectiveness of FS in reducing seroma volume. In addition, this study also showed increased flap adherence to the muscle bed 7 days post surgery (Harada et al., 1992).

Carrier for Growth Factors and Chemotherapeutics

The fibrous network in a FS clot can act as a drug delivery devise that can be applied to a specific location. Additives can be "trapped" in the FS or enzymatically cross linked to the fibrin. This type of application appears quite promising. ThE results of several published studies are summarised below:
1. An endothelial growth factor/FS mix induced site-directed angiogenesis from the aorta to the heart in a rat model assessed 9 weeks after implantation (Fasol et al., 1994).
2. The anticancer drug MMC was conjugated with FS. Slow release was noted, as well as a therapeutic effect on a malignant tumour in a mouse model. The complex was safe for normal tissues (Yano et al., 1995).
3. A rabbit auto-transplant model was used to show that a deposit of FGF-b and FS increased revascularisation of ischaemic airway from omentum, and thus results in improved epithelial preservation of a tracheal autograft (Albes et al., 1994).
4. An acidic FGF-FS mix supports regeneration of some nerve fibres when placed with human Schwann cells to span a mid-thoracic spinal cord transection in a nude rat model (Guest et al., 1997).

The rat mastectomy model was used to verify that a rationally formulated rhFS containing rhFbgn, rhThrombin and rhFXIII is functional in vivo. This is the first pre-clinical demonstration of the efficacy of a totally recombinant human fibrin sealant (rhFS). This model is well established, and correlates with clinical efficacy. This model uses rhFS as a haemostat, a space filling agent, and a glue to secure the skin flap. Additionally, it is a chronic, rather than an acute, model. This model provides a substantial challenge to test the efficacy of rhFS. Experimental results are presented in the examples.

In summary, therefore, fibrin sealant prepared in accordance with the invention from three, purified, well characterised, recombinant components is a functional product. Compaction assays, thromboelastography (TEG), and optical density (OD) measurements demonstrate that the choice of formulation buffer can significantly affect the functional properties (and gel structure) of the rhFS. TEG, parallel plate rheometry, and tensile adhesion assays demonstrate that rhFXIII significantly increases rigidity, rupture strength, and adhesive strength of rhFS. Fibrinolysis assays demonstrate that rhFXIII decreases the degradation rate of rhFS. However, tensile adhesion tests, and literature regarding fibrinolysis rates, suggest that the beneficial effect of rhFXIII can be modulated by changes in formulation buffer and gel structure. Finally, in vivo experiments using a rat mastectomy model demonstrate the efficacy of a rationally determined formulation of rhFS in a proven animal model. This is the first demonstration of efficacy of a totally recombinant Fibrin Sealant.

The invention is illustrated by the following non-limiting examples.
1. Determination of Fibrinogen Concentration using Absorbance
2. Determination of Thrombin Concentration using a Chromogenic Activity Assay
3. Determination of Thrombin Concentration using a Clotting Assay
4. Determination of Factor XIII Concentration using ELISA
5. Determination of % Clottable Fibrinogen
6. Preparation of Concentrated Fibrinogen Solutions using Ethanol Precipitation
7. Determination of Resistance to Synersis using Compaction
8. Determination of Gelation Rate and Gel Properties by Thromboelastography (TEG)
9. Determination of Gelation Rate and Gel Properties by Optical Density measurements
10. Determination of Gelation Rate and Gel Properties by Parallel Plate Rheometry
11. Determination of Fibrinolysis Rate by Plasmin
12. Determination of Tensile Adhesive Strength of Fibrin Sealant
13. Rat Mastectomy Model

EXAMPLE 1

Determination of Fibrinogen Concentration using Absorbance

This method uses the Absorbance of a fibrinogen solution to determine the concentration of fibrinogen.

References
1. Mihalyi E., *Biochemistry*, 7(1):208–223 (1968)

Materials
TBS: 20 mM Tris pH7.4, 120 mM NaCl
rhFibrinogen 0.1 to 0.6 mg/ml in TBS
Quartz cuvette, 1 cm path length (Uvonic)
UV/Vis Spectrophotometer Procedure
1. Thaw the fibrinogen solution for 5–30 minutes at 37° C. Centrifuge at 14,000×g in an Eppendorf centrifuge for 5 min. Store at room temperature.
2. Dialyse the fibrinogen sample against TBS if the formulation buffer contains interfering components and cannot be matched for blanking the spectrophotometer.

3. Dilute the fibrinogen solution to 0.1 to 0.6 mg/ml so that $A_{280}$ is in the range of 0.1 to 0.9 AU.
4. Blank the spectrophotometer against the formulation buffer, and determine the concentration of the fibrinogen to be tested by measuring the Absorbance at 280 nm and 320 nm. [mg/ml Fbgn=$(A_{280}-A_{320})/1.51$]. The $A_{320}$ should be examined for signs of turbidity that would indicate that the fibrinogen solution is unstable and is aggregating.

EXAMPLE 2

Determination of Thrombin Concentration using a Chromogenic Activity Assay

This procedure describes an assay for amidolytic activity of thrombin. The release of p-nitroaniline from a synthetic substrate due to the enzymatic action of thrombin is followed by measuring the increase in Absorbance at 405 nm. Quantitation of thrombin is achieved by comparison of the rate of increase of Absorbance (v) with a standard curve under the same conditions. (Note: α-Thrombin, β-thrombin and γ-thrombin are all reported to be active towards chromogenic substrates, while their clotting activities vary.)

References

S Sonder and J Fenton II, "Thrombin Specificity with Tripeptide Chromogenic Substrates", *Clinical Chem.*, vol. 32, No. 6, 1986.

Materials

TBS/BSA buffer: 20 mM Tris pH7.4, 120 mM NaCl, 1 mg/ml BSA (Sigma)

hThrombin Standard (HT 1002a: Enzyme Research Laboratories) Store working stock dilution of thrombin at −80° C. in 25 mM Tris pH7.4, 50% glycerol. Suggest 100 μl/vial at 500 U/ml.

Spectrozyme TH substrate (H-D-HHT-L-Ala-L-Arg-pNA.2AcOH: American Diagnostica)

10% acetic acid solution 96-well microtitre plates (Nunc Maxisorp)

Plate reader for 96-well microtitre plates. (Molecular Devices)

Procedure

1. Daily, remove vial of working standard dilution from freezer and dilute with TBS/BSA to highest standard concentration of desired standard curve. (i.e. 20 μg/ml: 31.7 μl stock standard+968 μl TBS/BSA buffer)
2. Make 1:2 serial dilutions beginning with this standard for a total of at least 8 standards; 100 μl std+100 μl buffer.
3. Dilute samples and control in TBS/BSA buffer as desired to fall within standard curve range. Two or three dilutions of each sample are generally included.
4. Add 90 μl/well sample, standard, controls and buffer blank in duplicate to 96-well microtitre plate.
5. Dissolve 50 mM Spectrozyme TH chromogenic substrate in 10 ml dH$_2$O. Need 5 ml plate.
6. Add 50 μl/well substrate to plate.
7. Read $A_{405}$ kinetically for approx. 5 minutes or as desired. Alternately, allow colour to develop 7–10 minutes and stop reaction with 50 μl/well of 10% acetic acid before reading @ $A_{405}$. A linear standard curve may then be constructed plotting concentration vs. $A_{405}$. Report as U/ml thrombin activity. For kinetic assay, fit linear curve to plot of concentration vs. initial, linear velocity points (Δ mOD/min) and report as U/ml thrombin activity.

EXAMPLE 3

Determination of Thrombin Concentration using a Clotting Assay

Thrombin degradation products may show less clotting activity while having the same activity in the amidolytic (chromogenic) activity. It is therefore necessary to assay the clotting activity in final product thrombin. A simple assay was developed using the manual ST-4 clot detection instrumentation sold by American Bioproducts. This instrument uses individual disposable cuvettes at 37° C. and measures clot endpoint electromechanically. Each cuvette is given a small iron bead which swings constantly through the sample (thrombin) due to alternating polarity of an electromagnetic field. At constant viscosity, the motion remains constant. With the addition of fibrinogen and the onset of clot formation, the viscosity increases which decreases the ball movement. An algorithm uses the variation in oscillation amplitude to determine the initial clotting time. The instrument is primarily used in clinical labs for coagulation testing on plasma samples but is easily adapted for this type of assay.

Materials hThrombin Standard (HT 1002a: Enzyme Research Laboratories) Store working stock dilution of thrombin at −80° C. in 25 mM Tris pH7.4, 50% glycerol. Suggest 100 μl/vial at 500 U/ml.

HFibrinogen (cat.#FIB3; Pg and vWF and Fn depleted: Enzyme Research Labs)

TBS (20 mM Tris, 120 mM NaCl, pH7.4)

TBS+5 mM CaCl$_2$+0.1% BSA (Sigma)

ST-4 Clot Detection System (American Bioproducts)

General Procedure

1. Prepare fibrinogen solution daily to 0.25 mg/ml. Prewarm to 37° C.
2. Prepare thrombin samples and standard dilutions to linear range of 2.5 μg/ml to 0.078 μg/ml (approximately 7.7 to 0.1 U/ml).
3. Set up instrument to run in "fibrinogen" test mode. (detects softer clot endpoint)
4. Add 100 μl thrombin sample to cuvette. Incubate 2 minutes @ 37° C.
5. Add 100 μl fibrinogen with automated pipette to start timer and reaction. Measures seconds to clot.
6. Construct log/log standard curve and calculate sample concentrations of thrombin.

EXAMPLE 4

Determination of Factor XIII Concentration Using ELISA

This protocol is a modification of a standard FXIII ELISA protocol, and uses a polyclonal Ab raised against recombinant FXIII [A$_2$] for capture and the same pAb (biotinylated) for detection.

Materials

Rabbit anti-FXIII pAb (ZGIlot D4679, 2.81 mg/ml)

biotinylated Rabbit anti-FXIII pAb (0.891 mg/ml)

streptavidin-HRP (Pierce #21124)

rhFXIII standard (batch 9x)

OPD substrate (Sigma P8787)

30% hydrogen peroxide solution

ELISA A (coating solution): 0.1M Na$_2$CO$_3$ pH9.6

ELISA B (blocking buffer): PBS, 0.05% Tween 20, 1% BSA

ELISA C (washing buffer): PBS, 0.05% Tween 20

OPD diluent (colour development): 0.1M citrate pH5.0 (313 ml 0.1M Na citrate+187 ml 0.1M citric acid)

Stop solution: 1M H$_2$SO$_4$ 96-well ELISA plates (Nunc Maxisorp)

Plate reader for 96-well microtitre plates. (Molecular Devices)

Procedure

1. Dilute Rabbit anti-FXIII pAb (ZGI lot D4679, 2.81 mg/ml) to a final concentration of 1 μg/ml in ELISA A (10 ml/plate).

2. Add 100 µl/well to ELISA plates (Nunc Maxisorp) and incubate at 4° C. overnight.
3. Wash wells 5× with ELISA C (200 µl/well, 20 ml/plate/wash).
4. To block plates, add 200 µl/well (20 ml/plate) ELISA B and incubate at least 2 hr at 37° C. with shaking.
5. Wash wells 5× with ELISA C (200 µl/well).
6. Add samples and standards (100 µl/well) and incubated at least 2.5 hr at 37° C. with shaking.

The standard solution was made by adding 10 µg/ml FXIII into ELISA B or FXIII −/− plasma. (Since the assay is very sensitive, I make a 100–200 µg/ml intermediate stock of FXIII in PBS or water and verify the concentration using the $A_{280}$ ($_e$=1.47) prior to the final dilution. Two 1:20 serial dilutions (100 µl+1900+1900 µl) are made to bring the FXIII concentration into the working range of the assay followed by 7× 1:2 serial dilutions (200 µl+200 µl) to make the std curve. (1:400 to 1:25,600 correspond to 25 ng/ml to 0.4 ng/ml in the well). All dilutions are made in ELISA B. For routine use, we often use 3 dilutions of an unknown (for example 1:500, 1:1000, 1:2000) so that at least one will be in the linear response range of the assay is (~1–10 ng/ml).

7. Wash wells 5× with ELISA C (200 µl/well).
8. Dilute biotinylated Rabbit anti-FXIII pAb (0.891 mg/ml) to a final concentration of 1 µg/ml in ELISA B, add 100 µl/well (10 ml/plate), and incubate 1 hr at 37° C. with shaking.
9. Wash wells 5× with ELISA C (200 µl/well).
10. Dilute streptavidin-HRP (Pierce #21124) to a final concentration of 1 µg/ml in ELISA B, add 100 µl/well (10 ml/plate), and incubate 45 min at 37° C. with shaking.
11. Wash wells 5× with ELISA C (200 µl/well).
12. Dissolve OPD substrate (1 tablet [Sigma P8787] in 12.5 ml OPD diluent), and add 10 µl 30% $H_2O_2$ immediately prior to use.
13. Add 100 µl/well (10 ml/plate) OPD solution to the plate and watch for colour development (yellow/orange).
14. Stop colour development by adding 100 µl/well 1M $H_2SO_4$ (Assays take~1 min 45 sec to develop).
15. Read plate at 490 nm.

EXAMPLE 5

Determination of Percent Clottable Fibrinogen

This method compares the amount of Fbgn in a solution prior to clotting to the amount of unclotted protein left after the addition of thrombin and the amount of Fbgn in the washed clot in order to determine the percentage of the original Fbgn incorporated into the clot. The value based on the measurement of the unincorporated protein is less accurate since high quality fibrinogen preparations are 95% or more clottable, and there is too little protein remaining in solution to measure accurately. Absorbance is used to measure Fbgn concentrations. Note that the extinction coefficient for Fbgn is different depending on whether it is dissolved in buffered saline (TBS or PBS) or in an alkaline urea solution.

References
1. Blomback, Birger & Blomback, Margareta, *ARKIV FOR KEMI* Band 10 nr. 29, 1956.
2. Mihalyi E., *Biochemistry*, 7(1):208–223 (1968)

Materials
40% Urea in 0.2N NaOH (made fresh)
15 mM phosphate buffer pH6.5, 75 mM NaCl
TBS: 20 mM Tris pH7.4, 120 mM NaCl
rhFibrinogen 1.5 to 3.0 mg/ml in TBS
100 NIH units/ml hThrombin (diluted from 500 NIH stock in phosphate buffer)
150 mM NaCl
Quartz cuvette
UV-Vis Spectrophotometer Procedure
1. Determine the concentration of the Fbgn to be tested by measuring the Absorbance at 280 nm and 320 nm [mg/ml Fbgn=$(A_{280}-A_{320})/1.51$]. Adjust the concentration to 1.5–3.0 mg/ml with TBS if necessary.
2. Determine the absorbance of the staring Fbgn solution in the urea/NaOH solution. Add 100 µl of Fbgn solution to 1 ml of the urea/NaOH reagent. Measure the Absorbance at 282 nm (within 10 minutes if possible).*
   [mg/ml Fbgn=$(A_{282}-0.01)/0.148$] Note the change in wavelength and extinction coefficient.

*If read within 10 minutes the slope of the absorbance/concentration will pass through zero. The measurement is valid for up to 4 hrs but after 30 minutes the line will be offset from zero by 0.01 AU. The value 0.148 for the extinction coefficient includes a correction factor for the 1:11 dilution based on the 1% extinction coefficient of 16.17. This extinction coefficient is suitable for Fbgn from Cohn fraction 1 (EtOH ppt.) or greater purity in urea/NaOH.

3. To 1 ml of the starting Fbgn solution add: 2 ml of 15 mM phosphate buffer pH6.5, 75 mM NaCl and 0.15 ml of 100 NIH U/ml thrombin solution.
4. Allow the solution to clot for 2 hours at room temperature.
5. Synerise (compress) the clot by vortexing and pressing with a small spatula to expel the supernatant.
6. Decant the supernatant and measure the protein concentration as in step 1 [mg/ml Fbgn=$(A_{280}-A_{320})/1.51$].
7. Wash the clot three times with 0.15 M NaCl.
8. Dissolve the clot in 1 ml of urea/NaOH and 100 µl TBS. After it has dissolved, determine the concentration as described in step 2 [mg/ml Fbgn=$(A_{282}-0.01)/0.148$].
9. The concentration of unclotted Fbgn remaining in the supernatant (step 6) and the Fbgn in the clot (step 8) should account for 100% of the Fbgn in the starting solution.

EXAMPLE 6

Preparation of Concentrated Fibrinogen Solutions using Ethanol Precipitation

Precipitation using ethanol (EtOH) and low temperature is used to concentrate dilute fibrinogen solutions sufficiently for preparing Fibrin Sealant for in vivo or in vitro experiments. Numerous in vivo models for Fibrin Sealant call for final concentrations of fibrinogen to be in the 20–30 mg/ml range. This translates to 40–60 mg/ml Fibrinogen in the 2× working solution prior to mixing with the Thrombin solution. Concentrations of 60–70 mg/ml fibrinogen can be obtained routinely using EtOH precipitation.

While other precipitation methods are available (glycine or ammonium sulphate), the precipitation with EtOH is simpler and more rapid since the precipitating agent is easily removed.

Reference
Dahlstrom K K et al. *Plast Reconstr Surg* 1992; 89:968–72.

Materials
95% EtOH (EtOH should be without additives/contaminants)
TBSz* Dialysis buffer: (120 mM NaCl, 20 mM Tris, 0.02% $NaN_3$ pH7.4)
Brookfield TC500 refrigerated bath or a MeOH/$H_2O$/dry ice bath at −3.8° C.
Dialysis tubing: 10–14,000 MW cut-off
Refrigerated centrifuge Procedure
1. Determine the concentration of the fibrinogen to be concentrated by measuring the absorbance at 280 nm and 320 nm [mg/ml Fbgn=$(A_{280}-A_{320})/1.51$].

2. At room temperature add EtOH to the fibrinogen solution dropwise with gentle vortexing/mixing to a final concentration of 10% v/v EtOH.
3. Place the fibrinogen in the −3.8° C. bath for 35 minutes. If using a dry ice bath maintain the temperature with minimal fluctuations. Do not mix or disturb the tube(s) during the precipitation process.
4. Centrifuge solution at −3° C. at 2,500×g for 20 minutes.
5. Decant off the supernatant and measure the concentration of unprecipitated fibrinogen by measuring the absorbance at 280 nm and 320 nm [mg/ml Fbgn=$(A_{280}-A_{320})/1.51$]. Precipitation coefficiencies of >90% are typical.
6. Place the pellet into dialysis tubing. Warm to 37° C., and add a minimal amount of TBSz* dropwise over several hours to dissolve the pellet. Dialyse against TBSz* until pellet has dissolved, generally overnight (Fibrinogen from different sources may vary behaviour).
7. Collect the dissolved fibrinogen and determine the concentration by measuring the absorbance at 280 nm and 320 nm [mg/ml Fbgn=$(A_{280}-A_{320})/1.51$]. Final recoveries of 70% are typical.

* If the material is to be used in vitro, omit the NaN$_3$, sterile filter the fibrinogen prior to the EtOH precipitation, and perform all open operations in a laminar air-flow hood, using sterile buffers and tissue culture technique.

EXAMPLE 7

Determination of Resistance to Syneresis using Compaction

Compaction measures the compressibility of a fibrin sealant when subjected to a centrifugal force. The compressibility is expressed as the percentage of the original volume retained by the gel after centrifugation. The higher percentage of the original volume retained, the greater the resistance to compression (syneresis). Generally resistance to compressibility correlates with high elastic modulus, and high tensile strength. In this assay, two solutions: Fibrinogen +/−FXIII, and Thrombin+CaCl$_2$ are prepared so that they are 2× with respect to Fbgn, FXIII, Thrombin, and CaCl$_2$ concentrations, and 1× in the concentration of any additives (salt, sugar). The Thrombin concentration generally must remain below 3–5 U/ml (final concentration) to avoid premature clotting and allow the solution to be mixed and pipetted into the tubes.

Reference
Dhall et al, *Thromb Haemostas* 1976; 35:737–45
Materials
TBSz (20 mM Tris-HCl, 120 mM NaCl, 0.02% NaN$_3$),
rhFibrinogen solution (6 mg/ml in TBSz+rhFXIII at 2×concentration+additives at 1×concentration)
rhThrombin solution (2 U/ml in TBSz+40 mM CaCl$_2$ and additives at 1×concentration)
Lecithin, or non-stick cooking spray (PAM, American Home Foods)
500 μl Eppendorf tubes
Eppendorf centrifuge
1 cc tuberculin syringe with a 26 g needle
Procedure
1. Determine the concentration of rhFibrinogen and rhFXIII by measuring the absorbance at 280 nm and 320 nm [mg/ml rhFbgn=$[A_{280}-A_{320})/1.51$] and [mg/ml rhFXIII=$(A_{280}-A_{320})/1.49$].
2. Coat Eppendorf tubes (1.5 or 0.5 ml) with lecithin or PAM.
3. Prepare the fibrinogen solutions.
4. Prepare the thrombin solutions. Make any intermediate dilutions (typically 80 U/ml) of rhThrombin in TBSz containing 1% PEG. Prepare 2× rhThrombin working solutions fresh for each measurement.
5. Warm the solutions in a 37° C. water bath for 5 min.
6. Mix equal volumes (typically 250 μl each) of the fibrinogen solution and thrombin solution and pipette into the pre-weighed lecithin treated tubes.
7. Incubate the tubes for 1 hr in a 37° C. water bath.
8. Centrifuge the tubes at 8,000×g (10,000 rpm) for 45 seconds in an Eppendorf centrifuge at room temp.
9. Remove the fluid above the compressed sample with a pre-weighed 1 cc tuberculin syringe with a 26 g needle and re-weigh.
10. Calculate the % original volume retained=100* (weight of uncompressed gel-weight of fluid)/weight of uncompressed gel.

EXAMPLE 8

Determination of Gelation Rate and Gel Properties by Thromboelastography (TEG)

The TEG measures shear elasticity of a developing clot by means of an oscillating cup and a static pin embedded in the clot. "Stiffness", clot time and rate of gelation is determined. In this assay, two solutions: Fibrinogen+/−FXIII, and Thrombin+CaCl$_2$ are prepared so that they are 2× with respect to Fbgn, FXIII, Thrombin, and CaCl$_2$ concentrations, and 1× in the concentration of any additives (salt, sugar). The Thrombin concentration generally must remain below 3–5 U/ml (final concentration) to avoid premature clotting and allow the solution to be mixed and pipetted into the tubes.

Materials
TBSz (20 mM Tris-HCl, 120 mM NaCl, 0.02% NaN$_3$),
rhFibrinogen solution (6 mg/ml in TBSz+rhFXIII at 2×concentration+additives at 1×concentration)
rhThrombin solution (2 U/ml in TBSz+40 mM CaCl$_2$ and additives at 1×concentration)
Mineral oil
Thromboelastograph (Haemoscope Corp. Morton Grove Ill.)
Procedure
1. Determine the concentration of rhFibrinogen and rhFXIII by measuring the absorbance at 280 nm and 320 nm [mg/ml rhFbgn=$(A_{280}-A_{320})/1.51$] and [mg/ml rhFXIII=$(A_{280}-A_{320})/1.49$].
2. Prepare the fibrinogen solutions (225 μl is used for each TEG run).
3. Prepare the thrombin solutions. Make any intermediate dilutions (typically 80 U/ml) or rhThrombin in TBSz containing 1% PEG. Prepare 2× rhThrombin working solutions fresh for each measurement (225 ml is used for each TEG run).
4. Preheat the solutions in a 37° C. water bath for 5 minutes.
5. Add 200 μl of the thrombin solution to an Eppendorf tube. Start the TEG run, and add 200 μl of the fibrinogen solution and mix 4–6× depending on the thrombin level.
6. Quickly pipette 360 μl of the mixed sealant into the TEG cup using reverse pipetting to avoid bubbles.
7. Add several drops of mineral oil to each side of the cup to keep the sealant from drying out during the run. Collect data as needed 930–120 minutes).
8. Gel time (K), rate of gelation (Angle), and rigidity (Amplitude) are calculated and reported by the TEG software.

EXAMPLE 9

Determination of Gelation Rate and Gel Properties by Optical Density Measurements The association of fibrin monomers, following thrombin induced release of fibrinopeptides, leads to gelation which can be followed spectrophotometrically as an increase in Optical Density (Turbidity) over time. Gel time, rate of clot formation and maximum OD can be determined. The higher the OD, the thicker the fibrin fibres and the "coarser" the gel. In this assay, two solutions: Fibrinogen+/–FXIII, and Thrombin+CaCl$_2$ are prepared so that they are 2× with respect to Fbgn, FXIII, Thrombin, and CaCl$_2$, and 1× in the concentration of any additives (salt, sugar). TBSz+1× additives is the blank solution. The Thrombin generally must remain below 3–5 U/ml (final concentration) to avoid premature clotting and allow the solution to be mixed and pipetted into the cuvette. To start the assay, the two solutions are mixed in equal volume, and the OD of the sample is measured as a function of time.

Materials

TBSz (20 mM Tris-HCl, 120 mM NaCl, 0.02% NaN$_3$),
rhFibrinogen solution (6 mg/ml in TBSz+rhFXIII at 2× concentration+additives at 1× concentration)
rhThrombin solution (2 U/ml in TBSz+40 mM CaCl$_2$ and additives at 1× concentration)
Quartz Cuvette * (Uvonic)
UV-Vis spectrophotometer (Hewlett Packard 8452A Diode Array spectrophotometer or similar)

* If the fibrinogen concentration is 0.2 mg/ml a cuvette with a pathlength of 1 cm can be used. If the concentration is increased to 3.0 mg/ml Fbgn a cuvette with a pathlength of 1 mm is used.

Procedure

1. Determine the concentration of rhFibrinogen and rhFXIII by measuring the absorbance at 280 nm and 320 nm [mg/ml rhFbgn=$(A_{280}-A_{320})/1.51$] and [mg/ml rhFXIII= $(A_{280}-A_{320})/1.49$].
2. Determine the volume needed in the cuvette such that solution height is above the light path. This is the volume of each solution that will be needed for each measurement.
3. Prepare the fibrinogen solutions.
4. Prepare the thrombin solutions. Make any intermediate dilutions (typically 80 U/ml) of rhThrombin in TBSz containing 1% PEG. Prepare 2× rhThrombin working solutions fresh for each measurement.
5. Warm the solutions in a 37° C. water bath for 5 min.
6. Blank the spectrophotometer with a cuvette containing TBSz (+1× additives if present).
7. Mix the fibrinogen and thrombin solutions 1:1. Add the fibrinogen solution to an Eppendorf tube, add an equal volume of rhThrombin solution, and mix 4–6× with the pipette. Using reverse pipetting, dispense the needed volume into the cuvette in the spectrophotometer. Start taking readings as soon as the solutions are mixed. Measure absorbance (OD) as a function of time (approx. every 2 sec), at wavelengths 350–600 over time. The total monitoring time will depend on experimental endpoints and any additives that may alter clot parameters (10 min. is typical).

EXAMPLE 10

Determination of Gelation Rate and Gel Properties by Parallel Plate Rheometry

The Rheometer measures viscoelastic properties of a developing gel by means of an oscillating circular plate. Time-dependent measurements can be taken at very small levels of deformation (% strain) so that the gel structure is not damaged. In addition, the level of deformation and consequently the amount of applied force (Stress) can be increased until the gel ruptures to obtain a measure of cohesive strength. In this assay, two solutions: Fibrinogen+/–FXIII, and Thrombin+CaCl$_2$ are prepared so that they are 2× with respect to Fbgn, FXIII, Thrombin, and CaCl$_2$ concentrations, and 1× in the concentration of any additives (salt, sugar). Unlike the Thromboelastrograph, the parallel plate rheometer can measure the properties of fibrin sealant at full working concentration (~30 mg/ml Fibrinogen, final concentration). The Thrombin concentration generally must remain below 3–5 U/ml (final concentration) to avoid premature clotting and allow the solution to be mixed and pipetted into the tubes.

Materials

TBSz (20 mM Tris-HCl, 120 mM NaCl, 0.02% NaN$_3$),
TBSz+1% PEG-8000 (Fluka 81288)
rhFibrinogen solution (60 mg/ml in TBSz+rhFXIII at 2×concentration+additives at 1×concentration)
rhThrombin solution (2 U/ml in TBSz+40 mM CaCl$_2$ and additives at 1×concentration)
CSL$^2$-500 rheometer
2 cm Stainless Steel parallel plate geometry with solvent trap to keep the sample from drying out during the measurement Procedure 1. Equilibrate the rheometer to 37° C., zero and set gap to 100 μm. Re-zero after the instrument has equilibrated to 37° C., and confirm that the gap and volume to fill the gap correlate, otherwise re-zero.
2. Thaw rhFbgn for 10 min at 37° C., centrifuge at 14,000 rpm for 5 min in an Eppendorf centrifuge, and determine the concentration of rhFibrinogen and rhFXIII solutions by measuring the absorbance at 280 nm and 320 nm [mg/ml rhFbgn=$(A_{280}-A_{320})/1.51$] and [mg/ml rhFXIII= $(A_{280}-A_{320})/1.49$].
3. Prepare the fibrinogen solutions (20 μl is used for each TEG run).
4. Prepare the thrombin solutions. Make any intermediate dilutions (typically 80 U/ml) of rhThrombin in TBSz containing 1% PEG. Prepare 2× rhThrombin working solutions fresh for each measurement (20 μl is used for each TEG run).
5. Preheat the solutions in a 37° C. water-bath for 5 minutes.
6. Add 20 μl of the thrombin solution to an Eppendorf tube.
7. Add 20 μl of the fibrinogen solution, mix 4–6×, and pipette 32 μl into the fixed lower plate of the rheometer. Start the run. The lower plate will rise and the FS should fill the gap between the fixed lower plate, and the oscillating upper plate exactly. Typical settings are 2 cm parallel plates, 100 μm gap, 37° C., 1 Hz oscillations of 1% strain for 30 minutes, followed by oscillations of steadily increasing torque (and % strain) until the gel ruptures. Elastic modulus: G' (Pa) and loss modulus: G" (Pa) at 30 minutes, and oscillatory stress at rupture (Pa) are reported.

EXAMPLE 11

Determination of Fibrinolysis Rate by Plasmin

Fibrinolysis rates are used to investigate the effect of changes in formulation variables on gel structure and the rate of degradation of Fibrin Sealant. In general slower lysis rates in vitro correlate with slower degradation rates in vivo. Fibrin gels are prepared, suspended in dilute plasmin solutions, and rocked gently. At the beginning of the assay, there is negligible soluble protein in the sample other than the plasmin. As the gel is degraded by plasmin, soluble fragments of fibrin are released that can be measured by Absorbance of the solution after the gel is completely lysed.

In this assay, two solutions: Fibrinogen+/–FXIII, and Thrombin+CaCl$_2$ are prepared so that they are 2× with respect to Fbgn, FXIII, Thrombin, and $CaCl_2$ concentrations, and 1× in the concentration of any additives (salt, sugar). This assay uses fibrin sealant at full working concentration (~30 mg/ml Fibrinogen, final concentration). The Thrombin concentration generally must remain below 3–5 U/ml (final concentration) to avoid premature clotting and allow the solution to be mixed and pipetted into the tubes.

References

K R Seibenlist and M W Mosesson, *J. Biol Chem* (1994) 45(11), 28418–28419.

M W Edwards et al, *Fibrinolysis* (1993) 7, 211–216.

Materials

TBSz (20 mM Tris-HCl, 120 mM NaCl, 0.02% $NaN_3$),
rhFibrinogen solution (60 mg/ml in TBSz+rhFXIII at 2×concentration+additives at 1×concentration)
rhThrombin solution (2 U/ml in TBSz+40 mM $CaCl_2$ and additives at 1×concentration)
human Plasmin (Cat# Hplas: Enzyme Research Labs)
lysis buffer (50 mM Tris-HCl pH8.6, 10 mM $CaCl_2$)
Eppendorf tubes
1 cm pathlength Quartz Cuvette (Uvonic)
UV-Vis spectrophotometer (Hewlett Packard 8452A Diode Array spectrophotometer or similar)

Procedure

1. Determine the concentration of rhFibrinogen and rhFXIII by measuring the absorbance at 280 nm and 320 nm [mg/ml rhFbgn=$(A_{280}-A_{320})/1.51$] and [mg/ml rhFXIII= $(A_{280}-A_{320})/1.49$].
2. Prepare the fibrinogen solutions.
3. Prepare the thrombin solutions. Make any intermediate dilutions (typically 80 U/ml) of rhThrombin in TBSz containing 1% PEG. Prepare 2× rhThrombin working solutions fresh for each measurement.
4. Warm the solutions in a 37° C. water bath for 5 min.
5. Mix equal volumes (typically 20 µl each) of the fibrinogen solution and thrombin solution in an Eppendorf tube.
6. Incubate the tubes overnight in a 37° C. water bath.
7. Using a spatula, carefully loosen the gels in each tube with minimal distortion.
8. Add 1.2 ml 8 µg/ml (approximately 0.2 cu/ml) plasmin solution to each tube. (The volume of plasmin solution added depends on the quantity of fibrin being lysed. Ideally, the absorbance of the solution after complete lysis will be ~0.9 AU without dilution.)
9. Rock the tubes gently at 37° C. to keep the gels floating freely. Lysis rates are dependent on the surface area of the gel that is exposed to plasmin, so the measurements will be invalid if the gel does not float freely.
10. Measure the Absorbance at 280 nm and 320 nm at specified time points.
11. Measure the Absorbance at 280 nm and 320 nm after the gel is completely lysed.
12. Calculate the % lysis at each time: % lysis=100* $(A_{280}-A_{320})$time t/$(A_{280}-A_{320})$ complete lysis.

EXAMPLE 12

Determination of Tensile Adhesive Strength of Fibrin Sealant

The tensile adhesive strength of fibrin sealant is measured by covering the opposed surfaces of two interlocking stainless steel jigs with the material that the sealant should adhere to (adherand). These surfaces are separated by thin spacers so that a known volume of sealant will fill the gap between the two adherands. Fibrin Sealant is placed between the adherand and allowed to gel. After gelation, the jigs are placed in a mounting fixture on an Instron materials testing apparatus. The jigs are then pulled apart at a constant rate, and the force generated is measured until the sealant fails and the jigs separate. In this assay, two solutions: Fibrinogen+/−FXIII, and Thrombin+$CaCl_2$ are prepared so that they are 2× with respect to Fbgn, FXIII, Thrombin, and $CaCl_2$ concentrations, and 1× in the concentration of any additives (salt, sugar). This assay can measure the properties of fibrin sealant at full working concentration (~30 mg/ml Fibrinogen, final concentration). The Thrombin concentration generally must remain below 3–5 U/ml (final concentration) to avoid premature clotting and allow the solution to be mixed and pipetted into the jigs.

Materials

TBSz (20 mM Tris-HCl, 120 mM NaCl, 0.02% $NaN_3$)
TBSz+1% PEG-8000 (Fluka 81288)
rhFibrinogen solution (60 mg/ml in TBSz+rhFXIII at 2×concentration+additives at 1×concentration)
rhThrombin solution (2 U/ml in TBSz+40 mM $CaCl_2$ and additives at 1×concentration)
Instron model 4501 Material testing apparatus
Custom stainless steel tensile jigs (2 cm diameter) and mounting fixtures
5 minute epoxy (Devcon)
0.005" thick matt finish Silastic sheet (Dow Corning), 6× extracted in chloroform, dried ON in hood Procedure 1. Using 5 minute epoxy, glue 2 cm discs of silastic (adherand) to the stainless steel jigs. Allow to set at least 30 min, and equilibrate the jigs to 37° C.
2. Thaw rhFbgn for 10 min at 37° C., centrifuge at 14,000 rpm for 5 min in an Eppindorf centrifuge, and determine the concentration of rhFibrinogen and rhFXIII solutions by measuring the absorbance at 280 nm and 320 nm [mg/ml rhFbgn=$(A_{280}-A_{320})/1.51$] and [mg/ml rhFXIII= $(A_{280}-A_{320})/1.49$].
3. Prepare the fibrinogen solutions (20 µl is used for each jig).
4. Prepare the thrombin solutions. Make any intermediate dilutions (typically 80 U/ml) of rhThrombin in TBSz containing 1% PEG. Prepare 2× rhThrombin working solutions fresh for each measurement (20 µl is used for each jig).
5. Preheat the solutions in a 37° C. water bath for 5 minutes.
6. Place spacers in pre-warmed jigs. Typically jigs are prepared in sets of 6 and 3 sets (n=18) are tested for each condition.
7. Add 20 µl of the thrombin solution to an Eppendorf tube.
8. Add 20 µl of the fibrinogen solution, mix 4–6×, and pipette 32 µl onto the bottom jig, place the top jig on the sealant, and incubate 30 min at 37° C. A typical routine loads, then tests, three sets of 6 jigs at 10 minute intervals with an incubation time of 30 min.
9. After incubation, place the jigs 1 at a time in the Instron, and pull apart at a rate of 0.5 mm/min.
10. Visually check each jig after testing for any signs of misalignment of incomplete gap filling. Omit samples with visible flaws from further analysis.
11. Report ultimate tensile strength as the maximum force obtained per surface area of sealant ($g/cm^2$).

EXAMPLE 13

Rat Mastectomy Model

This model was originally developed and championed by W Spotnitx et al. at the University of Virginia. Male Sprague-Dawley rats weighting 320–370 grams were anaesthetised with sodium pentobarbital. A midline incision was made from the sternal notch to xiphoid process. The skin was separated from the left pectoralis muscle, creating a subcutaneous pocket. An incision was made along the pectoralis just left of the sternal midline. The pectoralis was retracted, exposing the arm pit. Lymphatic tissue and nodes (2–3) were excised, followed by removal of the pectoralis. If haemorrhage occurred, the vessel was ligated with 4-0 silk suture. The undersurface of the skin flap was disrupted (60 scrapes) with a #22 scalpel blade to traumatise the subcutaneous lymphovasculature. Fibrin sealant (1.2 ml) or vehicle was then applied to the pocket, undersurface of the skin and on the rib cage. The skin was closed with 4-0 silk, using a continuous suture followed by interrupted sutures. Animals were sacrificed 5 days later and the fluid aspirated. The cavity was opened to inspect for residual fluid and harvested for histopathological evaluation.

The model was first optimised and tested using FS prepared with plasma-derived Fbgn and rhThrombin. In the pilot experiment, FS significantly reduced seroma volumes from 5.9 ml±3.2 to 1.5 ml±1.4 (p<0.0008). Unlike the experience of the UVa group, no dehiscence of the wound was observed in any animal. This was attributed to modification of the suturing technique in our model, similar to that reported by Harada et al., 1992.

Figure 15:
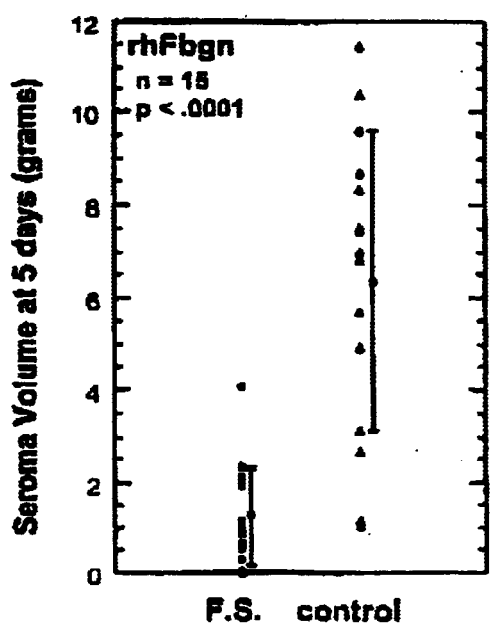
FIG. 15 is a plot demonstrating the efficacy of rhFS in reducing the seroma volume after a radical mastectomy in rates. This is the first pre-clinical demonstration of the efficacy of a totally recombinant human fibrin sealant. Th weight of the seroma fluid at day 5 is reported. The error bars represent standard deviation. Conditions of the assay: TBS (20 mM Tris-HCl, pH7.4, 120 mM NaCl), 4.5% sucrose, 20 mM CaCl$_2$, 30 mg/ml rhFibrinogen, 287.5 U/ml rhThrombin, and 300 $\mu$g/ml rhFXIII/mg rhFbgn.

After the TBS+4.5% sucrose was identified as a formulation buffer for rhFS, rhFS was tested in the same model. The vehicle was TBS+4.5% sucrose and the rhThrombin concentration was increased from 250 to 287.5 U/ml (final) to compensate for slower clot times due to the sucrose. Otherwise, the two experiments were identical. The rhFS dramatically reduced fluid accumulation 5 days after surgery, when compared to a vehicle control (FIG. 15). Seroma volumes were decreased from 6.4 ml±3.2 to 1.2 ml±1.1 (p<0.0001). No inflammation was associated with the rhFS, nor were any abnormal parameters noted histologically in the wound bed. Additionally, even though no antifibrinolytic agents are present in the rhFS formulation, the sealant was relatively intact 5 days post surgery.

REFERENCES

1. Lipinska I, Lipinski B, Gurewich V. *J Lab Clin Med* 1974; 84(4):509–16.
2. Hasegawa N, Sasaki S. *Thromb Res* 1990; 57(2):183–95
3. Siebenlist K R, Meh D A, Mosesson M W. *Biochemistry* 1996; 35(32):10448–53.
4. Clark R A, Lanigan J M, DellaPelle P, et al. *J Invest Dermatol* 1982; 79(5):264–9.
5. Redl H, Schlag G. In Schlag G, Redl H, eds. Fibrin Sealant in Operative Medicine. Berlin: Springer-Verlag, 1986. pp. 27–38.
6. Sierra D H. *J Biomater Appl* 1993; 7(4):309–52.
7. Siedentop K H, Harris D M, Sanchez B. *Laryngoscope* 1988; 98(7);731–3.
8. Siedentop K H, Park J J, Sanchez B. *Arch Otolaryngol Head Neck Surg* 1995; 121(7):769–72.
9. Park J J, Siedentop K H, Chung S, et al. *Am J Otol* 1997; 18(5):655–9.
10. Siedentop K H, Chung S E, Park J J, et al. *Am J Otol* 1997; 18(5):660–4.
11. Kjaergard H K, Weis-Fogh U S. *Eur Surg Res* 1994: 26(5):273–6.
12. Edwards M W, de Bang E, Strout J, Bishop P D. *Fibrinolysis* 1993; 7:211–216.
13. Siebenlist K R, Mosesson M W. *J Biol Chem* 1994; 269(45):28414–9.
14. Shulman S, Ferry J D. *J. Am. Chem. Soc.* 1949; 71:66–79.
15. Radosevich M, Goubran H I, BurnoufT. *Vox Sang* 1997; 72(3):133–43.
16. Jackson M R, MacPhee M J, Drohan W N, Alving B M. *Blood Coagul Fibrinolysis* 1996; 7(8):737–46.
17. Yorifuji H, Anderson K, Lynch G W, et al. *Blood* 1988; 72(5): 1645–50.
18. Nair C H, Shats E A. [In Process Citation]. *Thromb Res* 1997; 88(4):381–7.
19. Marx G, Blankenfeld A. *Blood Coagul Fibrinolysis* 1993; 4(1):73–8.
20. Nowotny R, Chalupka A, Nowotny C, Bosch P. In Winter G, Gibbos D, Plenk J J, eds. Biomaterials 1980: John Wiley and Sons Ltd., 1982.
21. Arnaud E, Morieux C, Wybier M, de Vernejoul M C. *Ann Chir Plast Esthet* 1994; 39(4): 491–8.
22. Lasa C, Jr., Hollinger J, Drohan W, MacPhee M. *Plast Reconstr Surg* 1995; 96(6):1409–17; discussion 1418.
23. Kania R E, Meunier A, Hamadouche M, et al. *J Biomed Mater Res* 1998; 43(1):38–45.
24. Nabeshima Y, Kurosaka M, Yoshiya S, Mizuno K. *Knee Surg Sports Traumatol Arthrosc* 1995; 3(1):34–8.
25. Xu W, Li H, Brodniewicz T, et al. *Burns* 1996; 22(3): 191–6.
26. Auger F A, Guignard R, Lopez Valle C A, Germain L. *Br J Plast Surg* 1993; 46(2):136–42.
27. Jabs A D, Jr., Wider T M, DeBellis J, Hugo N E. *Plast Reconstr Surg* 1992; 89(2):268–71.
28. Kram H B, Hino S T, Harley D P, et al. *J Biomed Mater Res* 1986; 20(5):547–53.
29. Kuzu A, Aydintug S, Karayalcin K, et al. *J R Coll Surg Edinb* 1992; 37(3): 162–4.
30. Raccuia J S, Simonian G, Dardik M, et al. *Am J Surg* 1992; 163(2):234–8.
31. Kjaergard H K, Axelsen P, Weis-Fogh U S. *Injury* 1995; 26(3):147–9.
32. Larson M J, Bowersox J C, Lim R C, Jr., Hess J R. *Arch Surg* 1995; 130(4):420–2.
33. Brown D M, Barton B R, Young V L, Pruitt B A. [published errata appear in *Arch Surg* July 1992; 127(7): 822 and August 1992; 127(8):960]. *Arch Surg* 1992; 127(4):404–6.
34. De Iaco P, Costa A, Mazzoleni G, et al. *Fertil Steril* 1994; 62(2):400–4.
35. Bold E L, Wanamaker J R, Zins J E, Lavertu P. *Am J Otolaryngol* 1996; 17(1):27–30.
36. Romanos G E, Strub J R. *J Biomed Mater Res* 1998; 39(3):462–8.
37. Lindenberg S, Lauritsen J G. *Ann Chir Gynaecol* 1984; 73(1):11–3.
38. Wang J Y, Goodman N C, Amiss L R, Jr., et al. *Ann Plast Surg* 1996; 37(4):400–5.
39. Moore M M, Mguyen D H, Spotnitz W D. *Am Surg* 1997; 63(1):97–102.
40. Sanders R P, Goodman N C, Amiss L R, Jr., et al. *J Surg Res* 1996; 61(1):65–70.
41. Lindsey W H, Masterson T M, Llaneras M, et al. *Am J Surg* 1988; 156(4):310–3.
42. Harada R N, Pressler V M, McNamara J J. *Surg Gynecol Obstet* 1992; 175(5):450–4.
43. Fasol R, Schumacher B, Schlaudraff K, et al. *J Thorac Cardiovasc Surg* 1994; 107(6): 1432–9.
44. Yano K, Mtsuoka H, Baba H, et al. *Gan To Kagaku Ryoho* 1995; 22(11):1629–31.
45. Albes J M, Klenzner T, Lotzerke J, et al. *Ann Thorac Surg* 1994; 57(2):444–9.
46. Guest J D, Hesse D, Schnell L, et al. *J Neurosci Res* 1997; 50(5):888–905.

47. Lindsey W H, Becker D G, Hoare J R, et al. *Laryngoscope* 1995; 105(3 Pt 1):241–3.

We claim:

1. A method for producing a fibrin sealant comprising mixing a human recombinant fibrinogen, recombinant human thrombin, recombinant human factor XIII and calcium ions together, wherein the fibrinogen is present at a concentration in solution of 20–30 mg/ml, the factor XIII is present in solution at a concentration of 3–10 µg of factor XIII per mg of fibrinogen present in solution, the thrombin is present in solution at a concentration of 5–300 I.U./ml, the calcium ions are present in solution at a concentration of 5–20 mM, and wherein sucrose is mixed at a concentration of about 4.5% with the fibrinogen, the factor XIII, the thrombin and the calcium.

2. A fibrin sealant produced according to the method of claim 1.

* * * * *